United States Patent
Ono et al.

(10) Patent No.: US 10,180,401 B2
(45) Date of Patent: Jan. 15, 2019

(54) SURFACE DEFECT DETECTING METHOD AND SURFACE DEFECT DETECTING APPARATUS

(71) Applicant: JFE Steel Corporation, Tokyo (JP)

(72) Inventors: Hiroaki Ono, Tokyo (JP); Toshifumi Kodama, Tokyo (JP); Takahiro Koshihara, Tokyo (JP); Akihiro Ogawa, Tokyo (JP); Yukinori Iizuka, Tokyo (JP)

(73) Assignee: JFE Steel Corporation (JP)

( * ) Notice: Subject to any disclaimer, the term of this patent is extended or adjusted under 35 U.S.C. 154(b) by 134 days.

(21) Appl. No.: 15/107,241

(22) PCT Filed: Dec. 24, 2014

(86) PCT No.: PCT/JP2014/084077
§ 371 (c)(1),
(2) Date: Jun. 22, 2016

(87) PCT Pub. No.: WO2015/098929
PCT Pub. Date: Jul. 2, 2015

(65) Prior Publication Data
US 2017/0122878 A1    May 4, 2017

(30) Foreign Application Priority Data

Dec. 27, 2013 (JP) ................................ 2013-270881
Apr. 25, 2014 (JP) ................................ 2014-090995
Apr. 25, 2014 (JP) ................................ 2014-090996

(51) Int. Cl.
*G01N 21/00* (2006.01)
*G01N 21/88* (2006.01)
(Continued)

(52) U.S. Cl.
CPC ....... *G01N 21/8851* (2013.01); *G01B 11/245* (2013.01); *G01N 21/892* (2013.01);
(Continued)

(58) Field of Classification Search
CPC . G01N 21/8851; G01N 21/952; G01N 21/956
(Continued)

(56) References Cited

U.S. PATENT DOCUMENTS 4,162,126 A * 7/1979 Nakagawa ........... G01N 21/952
250/559.46
5,949,901 A   9/1999 Nichani et al.
(Continued)

FOREIGN PATENT DOCUMENTS

EP    0 898 163      2/1999
JP    59-052735 A    3/1984
(Continued)

OTHER PUBLICATIONS

Korean Office Action dated Apr. 10, 2017, of corresponding Korean Application No. 10-2016-7016851, along with a Concise Statement of Relevance of Office Action in English.
(Continued)

*Primary Examiner* — Kevin Pyo
(74) *Attorney, Agent, or Firm* — DLA Piper LLP (US)

(57) ABSTRACT

A surface defect detecting method of optically detecting a surface defect of a steel material includes: an irradiation step of irradiating an examination target part with illumination light beams from different directions by using two or more distinguishable light sources; and a detection step of obtaining images by reflected light beams of the respective illumination light beams and detecting a surface defect in the examination target part by executing subtraction processing between the obtained images.

7 Claims, 20 Drawing Sheets

(51) Int. Cl.
| | |
|---|---|
| *G01N 21/892* | (2006.01) |
| *G01N 21/952* | (2006.01) |
| *G06T 7/70* | (2017.01) |
| *G06K 9/46* | (2006.01) |
| *G06K 9/62* | (2006.01) |
| *G06T 7/00* | (2017.01) |
| *H04N 7/01* | (2006.01) |
| *G01B 11/245* | (2006.01) |

(52) U.S. Cl.
CPC ......... *G01N 21/952* (2013.01); *G06K 9/4604* (2013.01); *G06K 9/6267* (2013.01); *G06T 7/0004* (2013.01); *G06T 7/70* (2017.01); *H04N 7/01* (2013.01); *G01N 2021/8822* (2013.01); *G01N 2021/8887* (2013.01); *G01N 2201/063* (2013.01); *G06T 2207/20224* (2013.01); *G06T 2207/30164* (2013.01)

(58) Field of Classification Search
USPC ............ 250/559.42, 559.44, 559.45, 559.46; 356/237.2, 237.3, 237.5
See application file for complete search history.

(56) References Cited

U.S. PATENT DOCUMENTS

| | | | |
|---|---|---|---|
| 6,097,482 | A | 8/2000 | Smith et al. |
| 6,327,374 | B1 | 12/2001 | Piironen et al. |
| 7,573,586 | B1 | 8/2009 | Boyer et al. |
| 8,179,524 | B2 | 5/2012 | Hayashi et al. |
| 9,743,008 | B2* | 8/2017 | Eisen ............... H04N 5/235 |
| 2001/0030744 | A1 | 10/2001 | Chang |
| 2002/0009218 | A1 | 1/2002 | Chapman et al. |
| 2009/0196489 | A1 | 8/2009 | Le |
| 2010/0319866 | A1 | 12/2010 | Avikainen et al. |

FOREIGN PATENT DOCUMENTS

| | | |
|---|---|---|
| JP | 11-037949 A | 2/1999 |
| JP | 2007-218889 | 8/2007 |
| JP | 2010-223621 A | 10/2010 |
| JP | 2011-117788 A | 6/2011 |
| JP | 2012-141322 | 7/2012 |
| JP | 2013-205332 | 10/2013 |
| RU | 2165612 | 4/2001 |
| RU | 2243540 | 12/2004 |

OTHER PUBLICATIONS

Supplementary European Search Report dated Apr. 19, 2017, of corresponding European Application No. 14873854.5.
Canadian Office Action dated May 1, 2017, of corresponding Canadian Application No. 2,934,796.
Office Action (pp. 12-15) dated Oct. 10, 2017, of corresponding Russian Application No. 2016129424, along with a Notice to Grant and a Concise Statement of Relevance of Office Action in English.
European Communication dated Dec. 23, 2016, of corresponding European Application No. 14873854.5.
Ferrari, R., "Enhanced Surface Inspection of Long and Flat Products with Pseudo-3D and Laser Sectioning Techniques," Danieli Automation, ISIS, 2013, 68 page presentation.
Ferrari, R., et al., "Enhanced Surface Inspection of Long roducts with Pseudo-3D Techniques," AISTech 2014 Proceedings, pp. 2581-2589.
Canadian Office Action dated Feb. 9, 2018, of corresponding Canadian Application No. 2,934,796.
Chinese Office Action dated Mar. 26, 2018, of corresponding Chinese Application No. 201480071110.5, along with a Concise Statement of Relevance of Office Action in English.

* cited by examiner

FIG. 14A
CONCAVE SHAPE
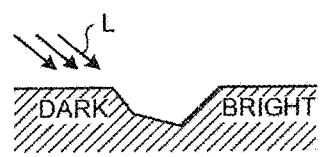
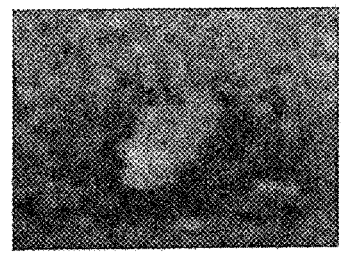
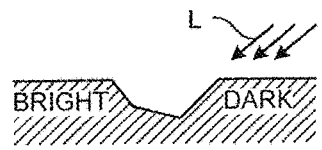
FIG. 14B
CONVEX SHAPE
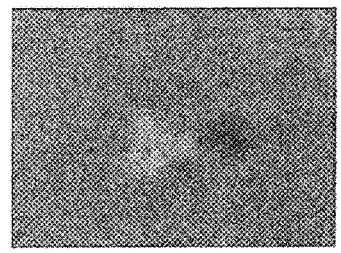
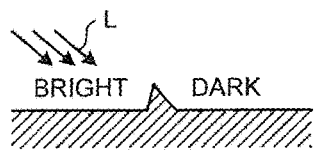
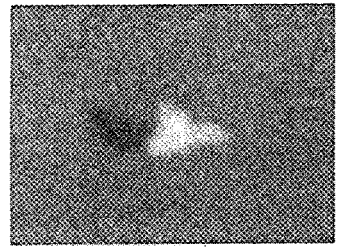
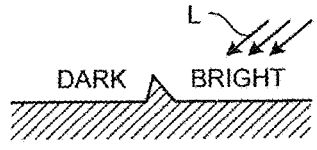

| SUBTRACTION IMAGE | BRIGHT PORTION IMAGE | DARK PORTION IMAGE | AREA RATIO | SIGNAL INTENSITY RATIO | CIRCULARITY OF BRIGHT PORTION | CIRCULARITY OF DARK PORTION | FEATURE AMOUNT DETERMINA-TION RESULT | MATCHING DETERMINATION WITH ACTUAL PRODUCT |
|---|---|---|---|---|---|---|---|---|
| | | | 0.88 | 0.79 | 0.68 | 0.755 | DEFECT | DEFECT |
| | | | 0.82 | 0.72 | 0.74 | 0.36 | DEFECT | DEFECT |
| | | | 0.54 | 0.62 | 0.67 | 0.40 | SOUND PORTION | SOUND PORTION |
| | | | 0.12 | 0.76 | 0.57 | 0.81 | SOUND PORTION | SOUND PORTION |

MAJOR AXIS-MINOR AXIS RATIO OF ELLIPSE

MAXIMUM FERET'S DIAMETER

CIRCULARITY AND CONVEX POLYGON FILLING RATE

| AREA ÷ SQUARE OF LENGTH OF CIRCUMFERENCE × 4π | AFTER CONVEX POLYGON FITTING, CALCULATE AREA RATIO |
|---|---|
| THE CLOSER TO CIRCLE, THE CLOSER TO 1 | SUBSTANTIALLY CLOSE TO 1 IF LINEAR |

FIG.26

| SUBTRACTION IMAGE | BRIGHT PORTION/ DARK PORTION IMAGE | MAJOR AXIS-SHORT AXIS RATIO | MAJOR AXIS ANGLE [deg] | FEATURE AMOUNT DETERMINATION RESULT | MATCHING DETERMINATION WITH ACTUAL PRODUCT |
|---|---|---|---|---|---|
| | | 0.07 | 54 | DEFECT | DEFECT |
| | | 0.08 | 66 | DEFECT | DEFECT |
| | | 0.59 | -33 | SOUND PORTION | SOUND PORTION |
| | | 0.82 | 12 | SOUND PORTION | SOUND PORTION |

SURFACE DEFECT DETECTING METHOD AND SURFACE DEFECT DETECTING APPARATUS

TECHNICAL FIELD

This disclosure relates to a surface defect detecting method and a surface defect detecting apparatus that optically detects a surface defect of a steel material.

BACKGROUND

In recent years, in manufacturing processes of steel products, in terms of improving yield through prevention of mass incompatibility, detection of surface defects of hot or cold steel materials has been demanded. Steel materials referred to herein mean: steel products including steel sheets and shaped steel such as seamless steel pipes, welded steel pipes, hot rolled steel sheets, cold rolled steel sheets, and thick plates; and semimanufactures such as slabs produced when these steel products are manufactured. Thus, a method has been proposed as a method of detecting a surface defect of a steel material, the method in which: a billet in a process of manufacturing a seamless steel pipe is irradiated with light; reflected light is received therefrom; and presence or absence of a surface defect is determined according to light quantity of the reflected light (see Japanese Patent Application Laid-open No. 11-037949). Further, a method has also been proposed in which: visible light beams of plural wavelength regions, which do not have mutual influence with emitted light radiated from a hot steel material and do not influence each other, are emitted from diagonal directions symmetrical to each other about a normal line of a surface of the hot steel material; an image by combined reflected light beams and images due to the individual reflected light beams are obtained in the normal direction of the surface of the hot steel material; and a surface defect of the hot steel material is detected from a combination of these images (see Japanese Patent Application Laid-open No. 59-052735).

According to the method described in JP '949, since reflectivity of a harmless pattern or scale is different from reflectivity of a base steel portion, the sound harmless pattern or scale may be erroneously detected as a surface defect. Therefore, in the method described in JP '949, by utilizing the fact that the shape of the defect is linear, the defect and the scale are distinguished from each other. However, surface defects on a steel material not only have linear shapes, but also various shapes such as circular shapes. Therefore, the method described in JP '949 is difficult to be applied to detection processing for a surface defect of a steel material. In the method described in JP '735, since there are a vast variety of defects, scale, harmless patterns and the like, scale or a harmless pattern is difficult to be distinguished from a surface defect just by a simple combination of images. Further, realistically, detection logic corresponding to the vast number of combinations of images is difficult to be constructed.

It could therefore be helpful to provide a surface defect detecting method and a surface defect detecting apparatus that enable scale or a harmless pattern to be accurately distinguished from a surface defect.

SUMMARY

Our surface defect detecting method of optically detecting a surface defect of a steel material includes: an irradiation step of irradiating an examination target part with illumination light beams from different directions by using two or more distinguishable light sources; and a detection step of obtaining images by reflected light beams of the respective illumination light beams and detecting a surface defect in the examination target part by executing subtraction processing between the obtained images.

The irradiation step includes a step of performing the irradiation with the illumination light beams by causing two or more flash light sources to repeatedly emit light such that light emission timings thereof do not overlap each other.

The irradiation step includes a step of simultaneously emitting illumination light beams of two or more light sources having wavelength regions not overlapping one another, and the detection step includes a step of obtaining images by reflected light beams of the respective illumination light beams by separating, by use of filters that transmit light beams having wavelengths that are the same as wavelengths of the illumination light beams, the reflected light beams of the respective illumination light beams that have been mixed with one another.

The irradiation step includes a step of simultaneously performing irradiation with illumination light beams of two light sources having linear polarization characteristics that are orthogonal to each other; and the detection step includes a step of obtaining images by reflected light beams of the respective illumination light beams by separating, by use of two polarization plates having linear polarization characteristics orthogonal to each other, the reflected light beams of the respective illumination light beams having been mixed with each other.

An angle of incidence of the illumination light beams of the respective light sources with respect to the examination target part is in a range of not smaller than 25° and not larger than 55°.

The detection step includes a step of adjusting, by using any of a half mirror, a beam splitter, and a prism, optical axes of plural imaging devices, which obtain images by reflected light beams of the respective illumination light beams, to be coaxial with one another.

The detection step includes a first determination step of extracting a bright portion and a dark portion of an image obtained by the execution of subtraction processing between the obtained images, and determining presence or absence of a concavo-convex surface defect from a positional relation between the extracted bright portion and dark portion and irradiation directions of the illumination light beams.

The first determination step includes a step of executing expansion processing with respect to images of the bright portion and the dark portion, and calculating a positional relation between the bright portion and the dark portion by extraction of an overlapping portion between the images of the bright portion and dark portion that have been subjected to the expansion processing.

The first determination step includes a step of executing binarization processing and labeling processing with respect to images of the bright portion and the dark portion, and calculating a positional relation between the bright portion and the dark portion by comparing positions of the centers of gravity of the images that have been subjected to the labeling processing.

The first determination step includes a step of calculating a positional relation between a bright portion and a dark portion by emphasizing the bright portion and the dark portion through filtering processing of images of the bright portion and dark portion.

The first determination step includes a step of: calculating, as a feature amount, at least one of a luminance ratio, an area ratio, and a circularity of the bright portion and dark portion, from a combination of the bright portion and the dark portion obtained by the calculation of the positional relation between the bright portion and dark portion; and determining, based on the calculated feature amount, presence or absence of a concavo-convex surface defect.

The detection step includes a second determination step of obtaining images by reflected light beams of the respective illumination light beams, extracting a bright portion and a dark portion of an image obtained by executing subtraction processing between the obtained images, calculating a shape feature amount that becomes an index of elongatedness of the extracted bright portion and dark portion, and determining, based on the calculated feature amount, presence or absence of an elongated defect.

The second determination step includes a step of calculating, as the shape feature amount, at least one of: a major axis-minor axis ratio according to elliptic approximation; a maximum Feret's diameter; a circularity; and a convex polygon filling rate.

The second determination step includes a step of determining the presence or absence of an elongated defect, based on, in addition to the shape feature amount, a direction of the bright portion and dark portion.

The second determination step includes a step of determining a direction of the bright portion and dark portion by using any of: a major axis-minor axis ratio according to elliptic approximation; a maximum Feret's diameter; and a linear filter.

Our surface defect detecting apparatus optically detects a surface defect of a steel material, and includes: an irradiation unit configured to irradiate an examination target part with illumination light beams from different directions by using two or more distinguishable light sources; and a detection unit configured to obtain images by reflected light beams of the respective illumination light beams and to detect a surface defect in the examination target part by executing subtraction processing between the obtained images.

The surface defect detecting apparatus optically detects a surface defect of a steel material, and includes: an irradiation unit configured to irradiate an examination target part with illumination light beams from different directions by using two or more distinguishable light sources; and a determination unit configured to obtain images by reflected light beams of the respective illumination light beams, to extract a bright portion and a dark portion of an image obtained by executing subtraction processing between the obtained images, and to determine presence or absence of a concavo-convex surface defect from a positional relation between the extracted bright portion and dark portion and irradiation directions of the illumination light beams.

The surface defect detecting apparatus optically detects a surface defect of a steel material, and includes: an irradiation unit configured to irradiate an examination target part with illumination light beams from different directions by using two or more distinguishable light sources; and a determination unit configured to obtain images by reflected light beams of the respective illumination light beams, to extract a bright portion and a dark portion of an image obtained by executing subtraction processing between the obtained images, to obtain a shape feature amount that becomes an index of elongatedness of the extracted bright portion and dark portion, and to determine, based on the calculated feature amount, presence or absence of an elongated defect.

By a surface defect detecting method and a surface defect detecting apparatus, scale or a harmless pattern is able to be accurately distinguished from a surface defect.

BRIEF DESCRIPTION OF THE DRAWINGS

FIGS. 14A and B are diagrams illustrating shade and shadow when light is emitted from one direction when surface shapes of parts to be examined are concave and convex.

FIG. 22 is a diagram illustrating results of surface defect detection processing of an example.

FIG. 26 is a diagram illustrating results of surface defect detection processing of an example.

REFERENCE SIGNS LIST

Figure 1:
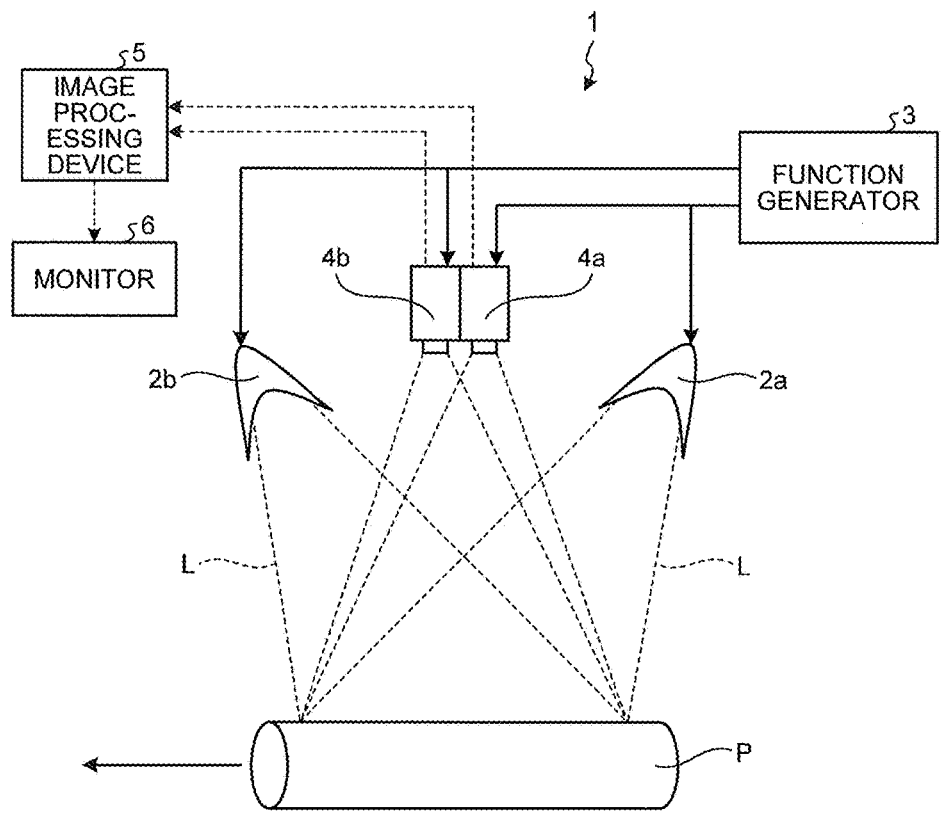
FIG. 1 is a schematic diagram illustrating a configuration of a surface defect detecting apparatus according to a first structure.

1 SURFACE DEFECT DETECTING APPARATUS
2a, 2b LIGHT SOURCE
3 FUNCTION GENERATOR
4a, 4b AREA SENSOR
5 IMAGE PROCESSING DEVICE
5 MONITOR
L ILLUMINATION LIGHT BEAM
P STEEL PIPE

DETAILED DESCRIPTION

Hereinafter, by referring to the drawings, configurations and operation of surface defect detecting apparatuses according to first to third structures will be described.

First Structure

By referring to FIG. 1 to FIG. 13, a configuration and operation of a surface defect detecting apparatus according to a first structure will be described.

Configuration of Surface Defect Detecting Apparatus

FIG. 1 is a schematic diagram illustrating the configuration of the surface defect detecting apparatus according to the first structure. As illustrated in FIG. 1, a surface defect detecting apparatus 1 is an apparatus that detects a surface defect of a steel pipe P, which is conveyed in a direction of an arrow illustrated in the figure, is cylindrically shaped, and the surface defect detecting apparatus 1 includes, as main components thereof, light sources 2a and 2b, a function generator 3, area sensors 4a and 4b, an image processing device 5, and a monitor 6.

The light sources 2a and 2b irradiate the same examination target part on a surface of the steel pipe P with distinguishable illumination light beams L, according to trigger signals from the function generator 3. The light sources 2a and 2b are desirably arranged symmetrically about the examination target part. Therefore, the light sources 2a and 2b are arranged such that the light sources 2a and 2b are displaced from a normal vector of the surface of the steel pipe P by the same angle, and that irradiation direction vectors of the illumination light beams L and the normal vector of the surface of the steel pipe P are on the same plane. The sameness of their angles of incidence mentioned herein aims to make the optical conditions as equal as possible to each other when the differently directed light sources are distinguished from each other, and to largely reduce a signal of a sound portion including scale and a harmless pattern by subtraction processing. Further, a signal of a sound portion largely depends on characteristics of a surface of a target, and the sameness is difficult to be unconditionally guaranteed by a certain angle. Therefore, when the angles are 25° to 55°, even if the angles are a little different from each other, as long as a signal of a sound part is able to be reduced by subtraction processing, the angles will be expressed as being the same. In this structure, the number of light sources is two, but as long as the light sources are distinguishable from one another, the number of light sources may be three or more. Distinguishable light sources mentioned herein refer to light sources for which a reflected light quantity is able to be found separately for each of the light sources with respect to reflected light beams obtained from a target.

The area sensors 4a and 4b capture two-dimensional images by reflected light beams of the illumination light beams L emitted from the light sources 2a and 2b according to trigger signals from the function generator 3. The area sensors 4a and 4b input data of the captured two-dimensional images to the image processing device 5. The area sensors 4a and 4b are desirably arranged on normal vectors of an examination target part as much as possible in a state where their respective imaging fields of view have been secured.

Figure 2:
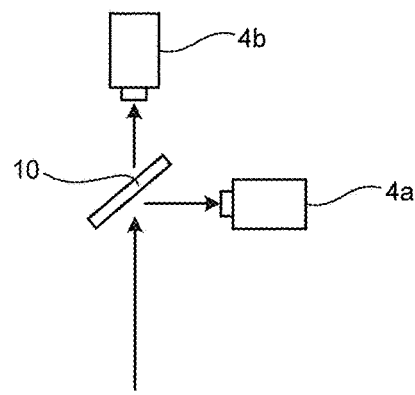
FIG. 2 is a schematic diagram illustrating a configuration of a modified example of area sensors illustrated in FIG. 1.

To solve a positioning problem, the area sensors 4a and 4b are made as close as possible to each other, and their optical axes are made as parallel as possible to each other. Further, as illustrated in FIG. 2, the optical axes of the area sensors 4a and 4b may be adjusted to be coaxial by use of any of a half mirror 10, a beam splitter, and a prism. Thereby, a later described subtraction image is able to be obtained accurately.

The image processing device 5 is a device that detects a surface defect in an examination target part, by executing later described subtraction processing between two two-dimensional images input from the area sensors 4a and 4b. The image processing device 5 outputs the two dimensional images input from the area sensors 4a and 4b and information related to a result of the surface defect detection to the monitor 6.

By executing surface defect detection processing described below, the surface defect detecting apparatus 1 configured as described above distinguishes scale or a harmless pattern from a surface defect in an examination target part. A surface defect mentioned herein refers to a concavo-convex defect. Further, scale or a harmless pattern means a portion having a surface film or surface characteristics with optical properties different from those of a base steel portion of a thickness of about several μm to several tens of μm, and is a portion that becomes a cause of noise in the surface defect detection processing. Hereinafter, surface defect detection processing according to first to third examples will be described.

First Example

First, by referring to FIG. 3 to FIG. 6, surface defect detection processing according to a first example will be described.

Figure 3:
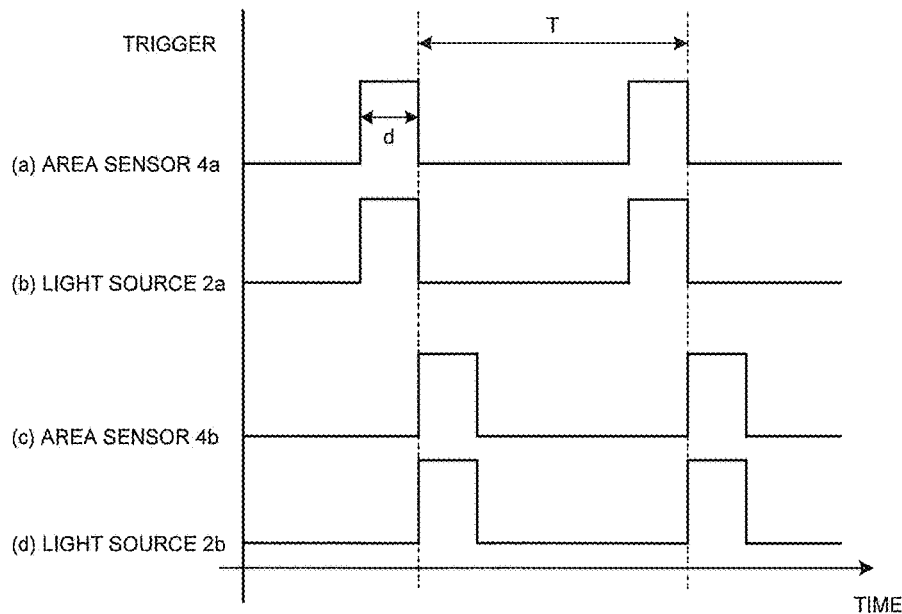
FIG. 3 is a timing chart illustrating driving timing of light sources and the area sensors illustrated in FIG. 1.

FIG. 3 is a timing chart illustrating driving timing of the light sources 2a and 2b and the area sensors 4a and 4b. In the figure, "d" represents a light emission duration of the light sources 2a and 2b, and "T" represents an imaging period for two dimensional images by the area sensors 4a and 4b. In the surface defect detection processing according to the first example, the light sources 2a and 2b are distinguished from each other, by the light sources 2a and 2b serving as flash light sources and these flash light sources being caused to repeatedly emit light such that their light emission timings do not overlap each other.

That is, as illustrated in FIG. 3, in this example, first, the function generator 3 transmits a trigger signal to the light source 2a and the area sensor 4a, the light source 2a emits the illumination light beam L, and the area sensor 4a completes capturing of a two-dimensional image within the duration d. After completion of the capturing of the two-dimensional image by the area sensor 4a, the function generator 3 transmits a trigger signal to the light source 2b and the area sensor 4b, and a two-dimensional image is captured similarly. According to this example, two dimensional images by the individual reflected light beams for the illumination light beams L emitted from the respective light sources are able to be captured with the time difference d and without reduction in light quantity.

If conveyance speed of the steel pipe P is fast, the light emission duration d of the flash light sources is desirably short. This is because, the shorter the light emission duration d is; the smaller the shutter delay between the two two-dimensional images obtained by the area sensors 4a and 4b becomes, and thus the smaller the positional displacement between the two-dimensional images due to the shutter delay is able to be made. Further, when detection of a surface defect by use of a subtraction image between the two-dimensional images by the individual reflected light beams is aimed, the light emission duration d of the flash light sources needs to satisfy a condition expressed by numerical expression (1):

Light emission duration $d$[sec]≤Minimum resolution [mm/pixel]×Allowable positional displacement [pixels]/Line conveyance speed [mm/sec] (1)

If, a size of a surface defect aimed to be detected is, for example, 20 mm, since empirically, signals of at least 5×5 pixels are needed to detect the surface defect, the resolution may be 4 mm/pixel. Further, in this case, the allowable positional displacement due to the irradiation timings of the illumination light beams L empirically needs to be not more than 0.2 pixel, and thus if the conveyance speed of the steel pipe P is 1, 3, or 5 m/s, the light emission duration of the light sources 2a and 2b needs to be not greater than 800, 270, or 160 μsec, respectively. If the conveyance speed and conveyance direction of the steel pipe P is constant, this positional displacement may be corrected after capturing the two-dimensional images.

In this mode, after executing image processing such as calibration, shading correction, noise removal and the like by use of camera parameters derived in advance for two-dimensional images input from the area sensors 4a and 4b, the image processing device 5 detects a surface defect in an examination target part, by executing subtraction processing between the two-dimensional images.

Specifically, if a luminance value of each pixel constituting a two-dimensional image Ia obtained when the illumination light beam L is emitted from the light source 2a is Ia(x, y) (where the number of pixels is X×Y, the x-coordinate is 1≤x≤X, and the y-coordinate is 1≤y≤Y) and a luminance value of each pixel constituting a two-dimensional image Ib obtained when the illumination light beam L is emitted from the light source 2b is Ib(x, y), a luminance value I_diff(x, y) of each pixel of their subtraction image I_diff is expressed by numerical equation (2):

$I\_diff(x,y)=Ia(x,y)-Ib(x,y)$ (2).

Examples of the two-dimensional images Ia and Ib capturing a surface defect, and scale and a harmless pattern, which are not defects, and their subtraction image I_diff are illustrated in FIGS. 4(a), (b), and (c), respectively. As illustrated in FIGS. 4(a), (b), and (c), in a sound portion, since an angle formed between the normal vector and the light source 2a equals an angle formed between the normal vector and the light source 2b despite the scale and the harmless pattern, the luminance value Ia(x, y)=the luminance value Ib(x, y), that is, the luminance value I_diff(x, y)=0. However, in a surface defect portion, since the surface has a concavo-convex shape, a site where the angle formed between the normal vector and the light source 2a does not equal the angle formed between the normal vector and the light source 2b is always present, and thus the luminance value Ia(x, y)≠the luminance value Ib(x, y), that is, the luminance value I_diff(x, y)≠0.

Therefore, by a subtraction device 11 generating a subtraction image between two two-dimensional images, scale and a harmless pattern, which are not defects, are removed, and only a surface defect is able to be detected. Only a surface defect is detected as described above, final evaluation of whether or not the surface defect is harmful is made through various feature amounts, and a result of the evaluation is displayed on the monitor 6.

If there is a positional displacement between the two two-dimensional images and this influences the subtraction image, a two-dimensional low pass filter is desirably used to reduce the influence of the positional displacement between the two-dimensional images. In this case, if the two-dimensional low pass filter is "H," a luminance value I'_diff(x, y) of the subtraction image is expressed by numerical equation (3):

$I'\_diff(x,y)=H*(Ia(x,y)-Ib(x,y))$ (3).

Further, preferably, as the light sources 2a and 2b, light sources that are the same are used, each of the light sources emits light so that the light becomes uniform parallel light as much as possible, and the examination target part is approximately planar. However, in application to when the surface is a little nonuniform or to a smooth curved surface like the steel pipe P, a surface defect is able to be detected by general shading correction.

Figure 5:
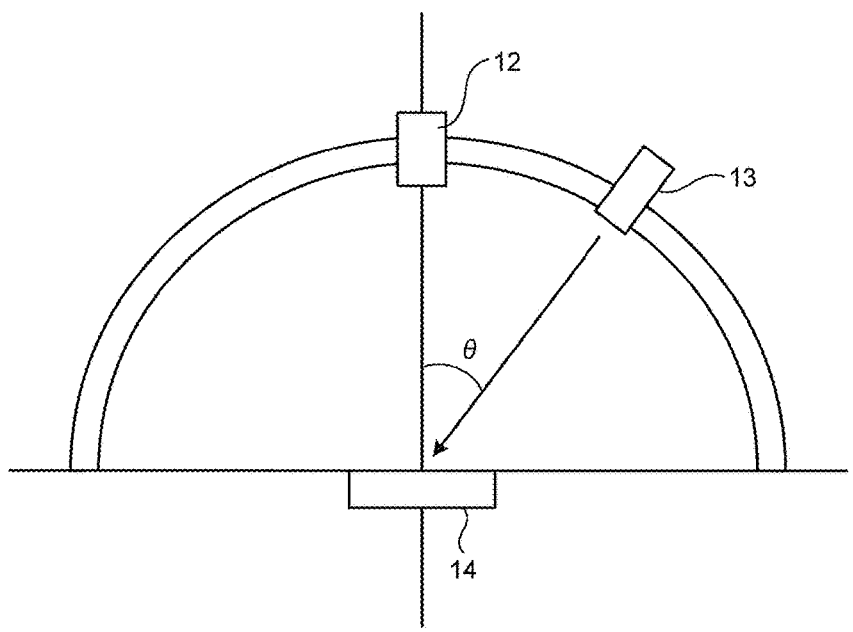
FIG. 5 is a schematic diagram illustrating a configuration of an apparatus used in an experiment to investigate the relationship between angle of incidence of an illumination light and reflectivity of a sound portion (base steel portion).
Figure 6:
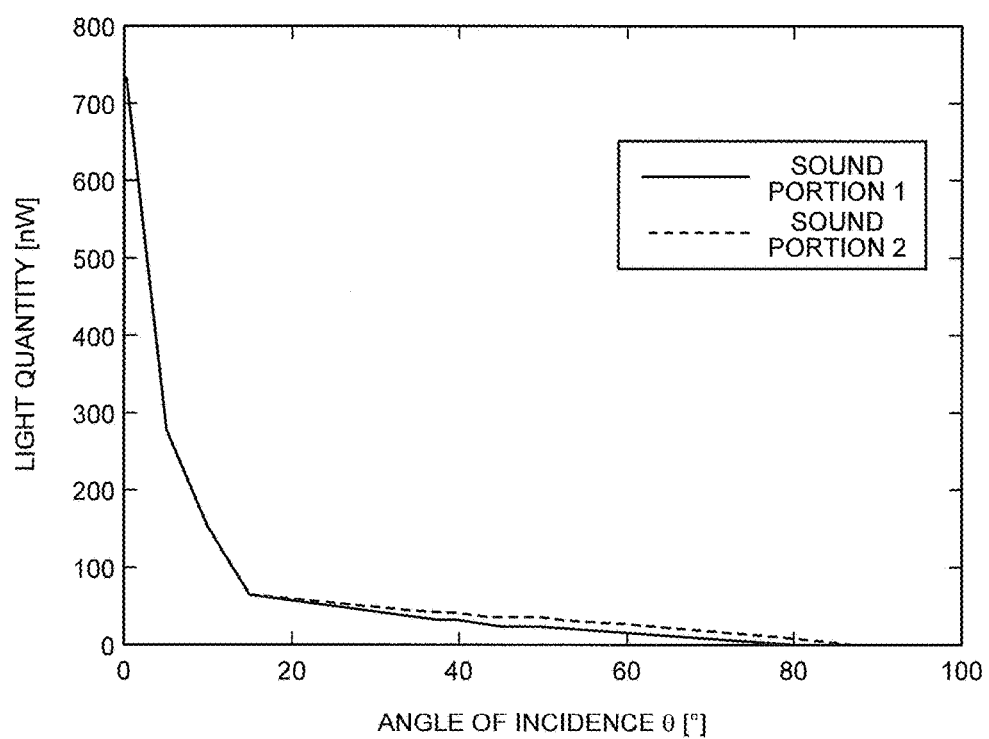
FIG. 6 is a diagram illustrating the relationship between angle of incidence of a laser and light quantity received by a power meter.

Further, the angle of incidence of the illumination light beams L is desirably in a range preventing a mirror reflection component from entering reflected light from a sound portion and enabling sufficient light quantity to be secured. We conducted an experiment to investigate the relationship between angle of incidence of the illumination light beams L and reflectivity of a sound portion (base steel portion). A configuration of an apparatus used in the experiment is illustrated in FIG. 5. As illustrated in FIG. 5, in this experiment, light quantity received by a power meter 12 when the power meter 12 was fixed to a position right above a slab sample 14 and angle of incidence θ of a laser 13 was changed from 0° to 90° was measured. Results of the experiment are illustrated in FIG. 6. As illustrated in FIG. 6, when the angle of incidence θ is in a range of 0° to 20°, the light quantity received by the power meter 12 is large due to inclusion of a mirror reflection component, but when the angle of incidence θ becomes not smaller than 60°, the light quantity received by the power meter 12 is largely reduced. Therefore, the angle of incidence of the illumination light beams L is desirably in a range of 25° to 55° with respect to a normal vector of an examination target part.

Depth direction resolution of an examination target part depends on an inclination angle of a defect and resolutions of the area sensors 4a and 4b. The inclination angle of a defect is an angle obtained by orthographically projecting "a normal vector of a defect portion" to "a plane formed of a light source direction vector and a normal vector of a surface of a sound portion of an examination target part," the angle formed between the orthographically projected vector and the normal vector of the surface of the sound portion. Although dependent on characteristics of the surface of the examination target part, when irradiation is performed with incident light at an angle of incidence of, for example, 45°, if the inclination angle of the defect is not smaller than about 10° with respect to the light source direction, it has been confirmed that a defect signal is detectable by subtraction processing. Therefore, if a resolution of one pixel is assumed to be 0.5 mm, theoretically, a depth direction resolution of about 0.5×tan 10°=0.09 mm is obtained.

Second Example

Next, by referring to FIG. 7, surface defect detection processing according to the second example will be described.

In the surface defect detection processing according to a second example, by using light sources having wavelength regions not overlapping each other as the light sources 2a and 2b, the light sources 2a and 2b are distinguished from each other. Specifically, as illustrated in FIG. 7, two types of wavelength selection filters 20a and 20b having wavelength regions not overlapping each other are arranged at the light sources 2a and 2b, and wavelength regions of the illumination light beams L are selected. Further, wavelength selection filters 21a and 21b having the same wavelength selection characteristics are arranged at the area sensors 4a and 4b.

According to this configuration, the reflected light beam of the illumination light beam L from the light source 2a is received only by the area sensor 4a through the wavelength selection filters 20a and 21a, and the reflected light beam of the illumination light beam L from the light source 2b is received only by the area sensor 4b through the wavelength selection filters 20b and 21b. Therefore, by matching imaging timings of the area sensors 4a and 4b to each other, two-dimensional images by the reflected light beams of the illumination light beams L from the light sources 2a and 2b are able to be captured without any positional displacement. Processing after capturing the two-dimensional images is similar to that of the first example.

When the moving speed of an examination target part is large, to prevent positional displacement due to the movement of the examination target part, by using flash light sources as the light sources 2a and 2b, imaging times of the two dimensional images may be shortened without changing irradiation timings of the light sources 2a and 2b. Further, a configuration may be adopted, in which, by capturing two-dimensional images by using a blue transmission filter as the wavelength selection filter 20a and a green transmission filter as the wavelength selection filter 20b and using a single color camera, only the reflected light beam of the illumination light beam L from the light source 2a is received in the blue channel and only the reflected light beam of the illumination light beam L from the light source 2b is received in the green channel.

Third Example

Figure 8:
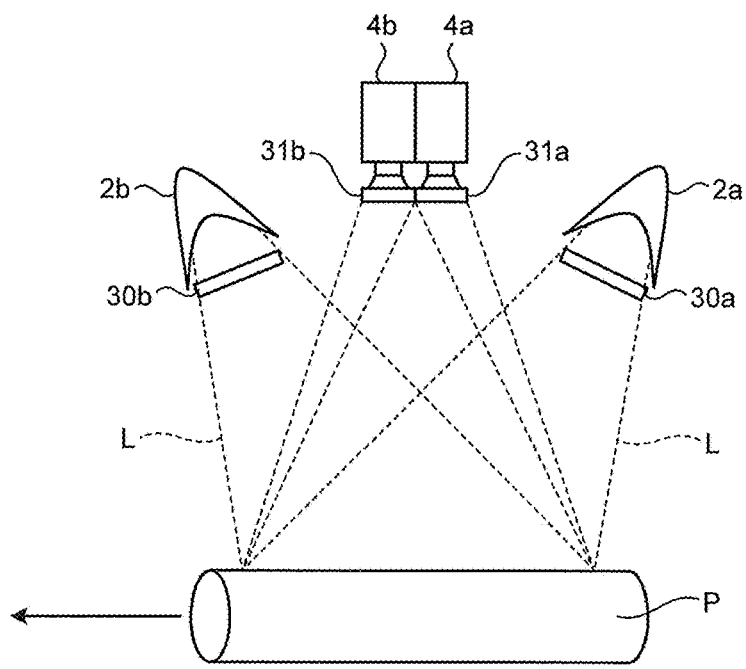
FIG. 8 is a schematic diagram for explanation of surface defect detection processing according to a third structure.

Next, by referring to FIG. 8, surface defect detection processing according to a third example will be described.

In the surface defect detection processing according to the third example, by using light sources having linear polarization characteristics orthogonal to each other as the light sources 2a and 2b, the light sources 2a and 2b are distinguished from each other. Specifically, as illustrated in FIG. 8, linear polarization plates 30a and 30b are arranged at α° and (α+90)° (where α is any angle) at the light sources 2a and 2b, and only light of polarization components orthogonal to each other is transmitted therethrough, respectively. A linear polarization plate means a filter that transmits only a linear polarization component of a certain direction, with respect to incident light. Further, linear polarization plates 31a and 31b having the same linear polarization characteristics as the linear polarization plates 30a and 30b are arranged at α° and (α+90°) at the area sensors 4a and 4b.

According to this configuration, the reflected light beam of the illumination light beam L from the light source 2a is received only by the area sensor 4a, and the reflected light beam of the illumination light beam L from the light source 2b is received only by the area sensor 4b. Therefore, by matching imaging timings of the area sensors 4a and 4b to each other, two-dimensional images by the reflected light beams of the illumination light beams L from the respective light sources are able to be captured without any positional displacement.

When the moving speed of an examination target part is large, by using flash light sources as the light sources 2a and 2b, imaging times of the two dimensional images may be shortened without changing irradiation timings of the light sources 2a and 2b. Positioning and processing after the capturing of the two dimensional images are similar to those of the first and second modes.

Example

Figure 9:
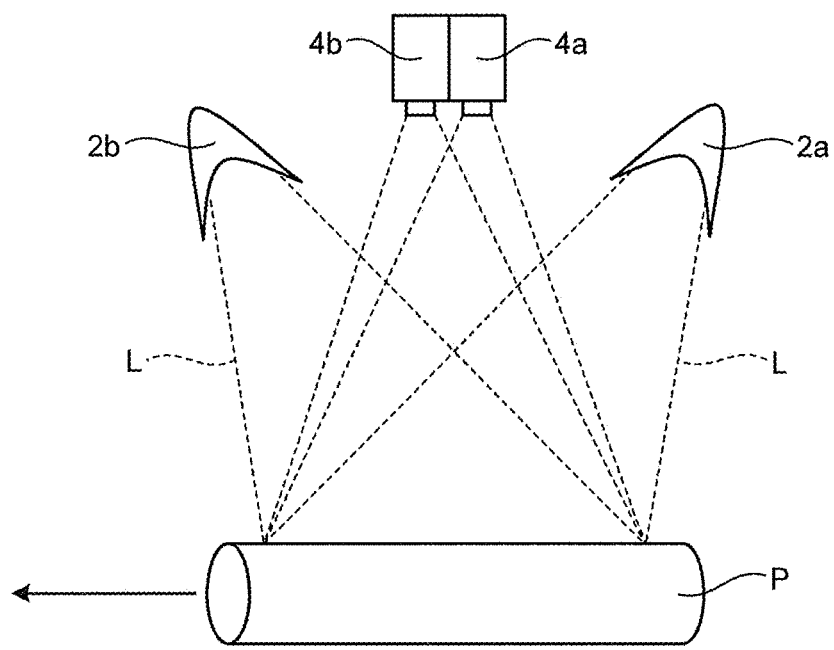
FIG. 9 is a schematic diagram illustrating a configuration of an apparatus used in an example.
Figure 10:
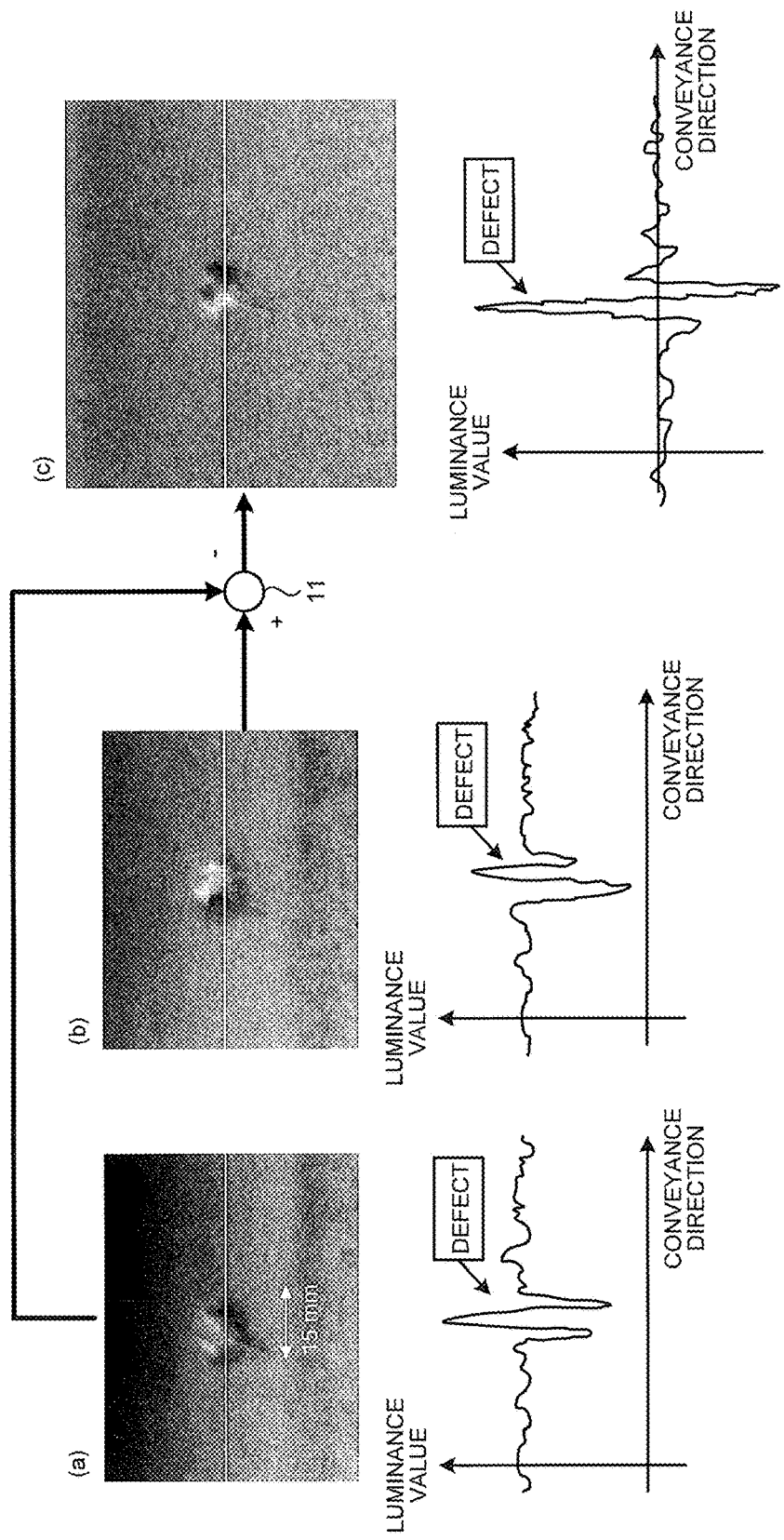
FIG. 10 is a diagram illustrating results of surface defect detection processing of the example.

In this example, as illustrated in FIG. 9, a surface defect of the steel pipe P was detected by use of a method of using flash light sources as the light sources 2a and 2b and changing light emission timings of the light sources 2a and 2b. Two-dimensional images were captured by arranging the area sensors 4a and 4b in a line, and positioning was performed by image processing. Results of the surface defect detection are illustrated in FIG. 10. FIG. 10(a) is a two-dimensional image upon irradiation with the illumination light beam L from the light source 2a, FIG. 10(b) is a two-dimensional image upon irradiation with the illumination light beam L from the light source 2b, and FIG. 10(c) is a subtraction image between the two-dimensional image illustrated in FIG. 10(a) and the two-dimensional image illustrated in FIG. 10(b). S/N ratios of the images illustrated in FIG. 10(a) to (c) were respectively 3.5, 3.5, and 6.0, and the SN ratio of the subtraction image improved as compared when the illumination light beam L was simply emitted from a single direction.

Figure 11:
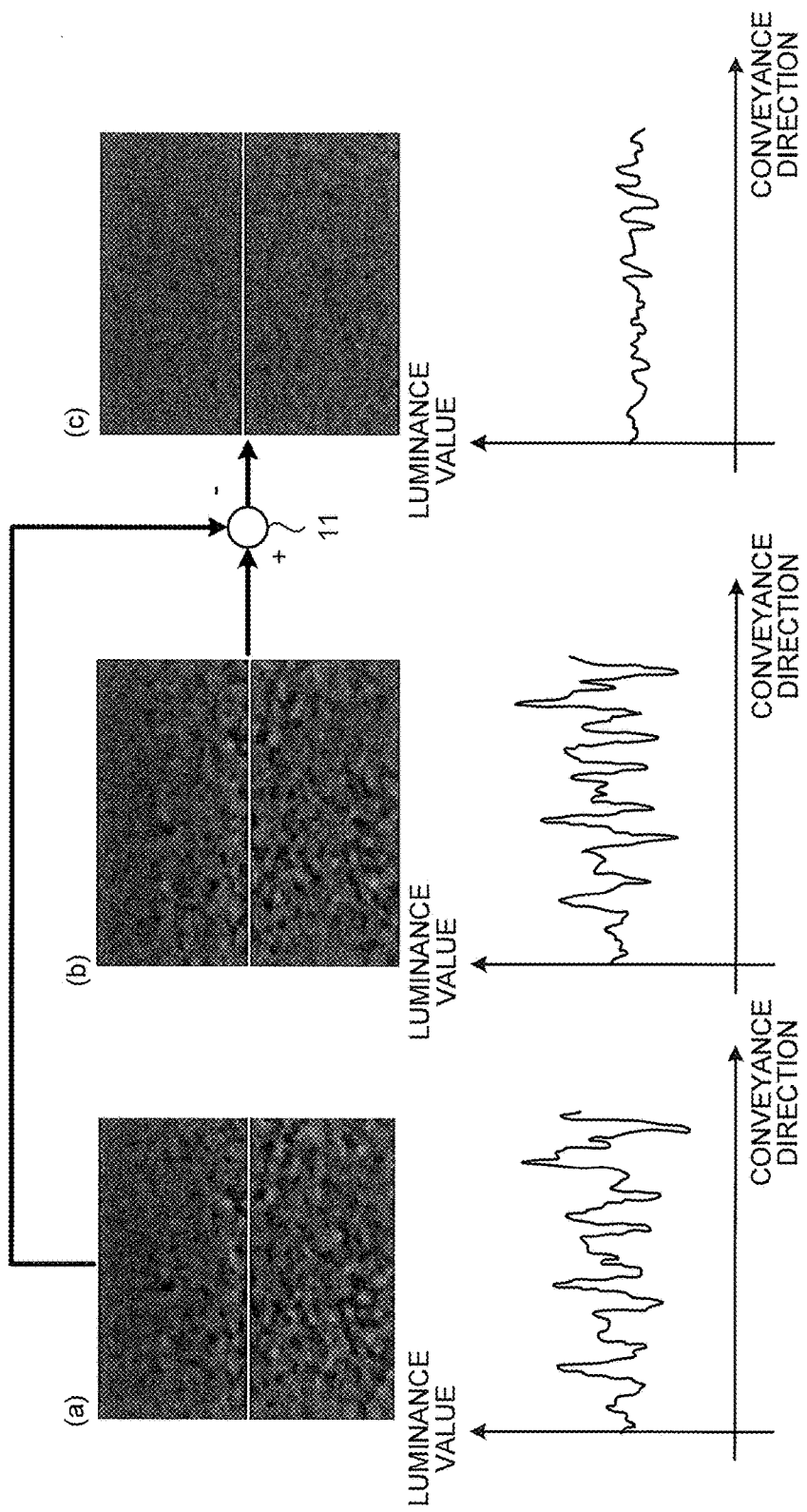
FIG. 11 is a diagram illustrating results of surface defect detection processing for a portion where scale has been generated.

FIG. 11 is a diagram illustrating results of surface defect detection processing with respect to a portion of the steel pipe, the portion where scale has been generated. FIG. 11(a) is a two-dimensional image upon irradiation with the illumination light beam L from the light source 2a, FIG. 11(b) is a two-dimensional image upon irradiation with the illumination light beam L from the light source 2b, and FIG. 11(c) is a subtraction image between the two-dimensional image illustrated in FIG. 11(a) and the two-dimensional image illustrated in FIG. 11(b). Black spots spread across the whole two-dimensional images illustrated in FIGS. 11(a) and (b) are the scale, which causes noise. Since the scale is flat shaped, by the obtainment of the subtraction image, the image of the scale was removed. Further, in the subtraction image, as compared with the case where the illumination light beam was simply emitted from a single direction, a signal of the scale, which causes noise, was reduced to about ¼.

First Modified Example

Figure 12:
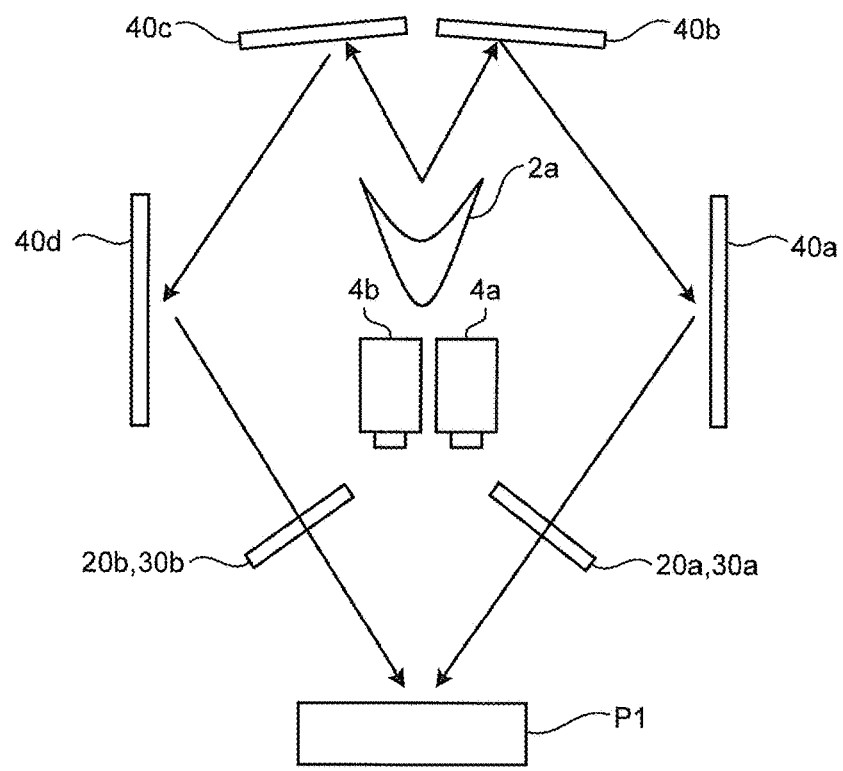
FIG. 12 is a schematic diagram illustrating a configuration of a modified example of the surface defect detecting apparatus according to the first structure.

FIG. 12 is a schematic diagram illustrating a configuration of a modified example of the surface defect detecting apparatus according to the first structure. As illustrated in FIG. 12, in this modified example, illumination light emitted from the single light source 2a is divided by plural mirrors 40a, 40b, 40c, and 40d, and an examination target part of a steel pipe P1 is finally irradiated with the illumination light beams from two directions. In this case, by arrangement of the wavelength selection filters 20a and 20b and the linear polarization plates 30a and 30b on the respective optical paths of the illumination light beams, effects similar to those of the second and third structures are able to be obtained. Although the illumination light beams are emitted from two directions in this modified example, the same applies to when illumination light beams are emitted from not less than three directions.

Second Modified Example

Figure 13:
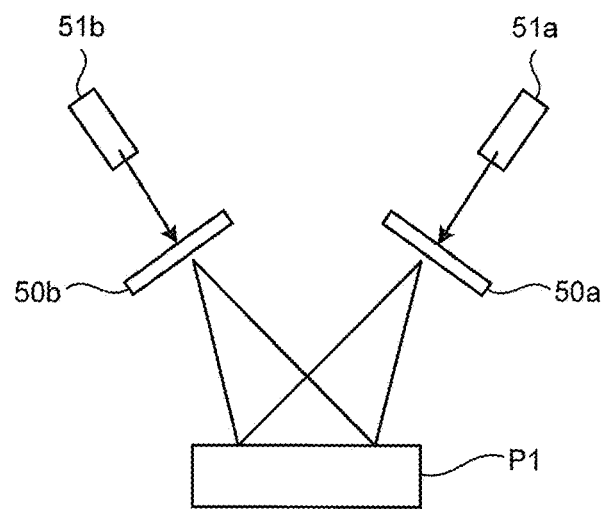
FIG. 13 is a schematic diagram illustrating a configuration of another modified example of the surface defect detecting apparatus according to the first structure.
Figure 15:
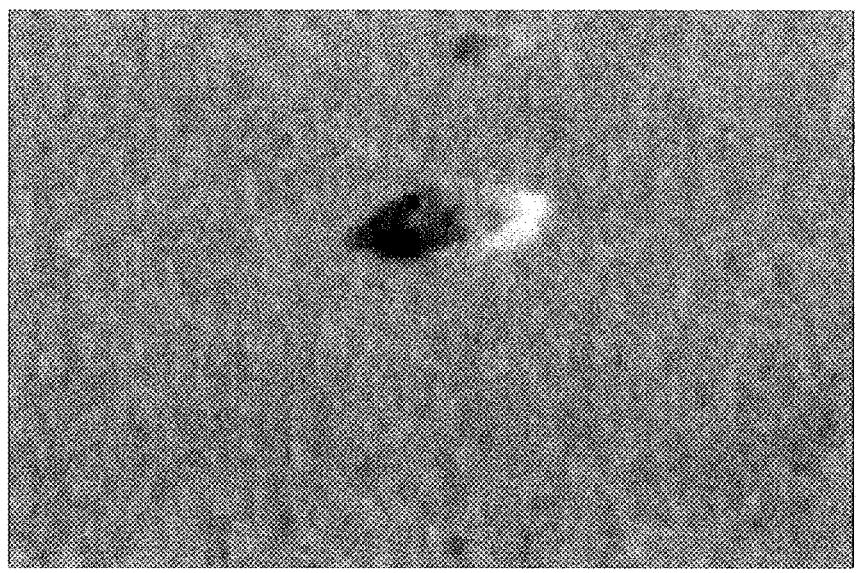
FIG. 15 is a diagram illustrating an example of a subtraction image of a concave shaped surface defect.

FIG. 13 is a schematic diagram illustrating a configuration of another modified example of the surface defect detecting apparatus according to the first structure. As illustrated in FIG. 13, in this modified example, instead of limiting wavelength of light sources by use of the wavelength selection filters 20a and 20b in the surface defect detecting apparatus illustrated in FIG. 7, wavelength of light sources is limited by use of pulse lasers 51 and 51b and diffusion plates 50a and 50b. In this modified example, the light sources are distinguished from each other by irradiation of an examination target part with laser light beams from the two pulse lasers 51a and 51b having wavelength regions different from each other, from left and right directions. The diffusion plates 50a and 50b are inserted in optical paths of the laser light beams for irradiation of the entire area of the examination target part with the laser light beams emitted from the pulse lasers 51a and 51b. Although the illumination light beams are emitted from two directions in this modified example, the same applies to when illumination light beams are emitted from not less than three directions.

Third Modified Example

Figure 7:
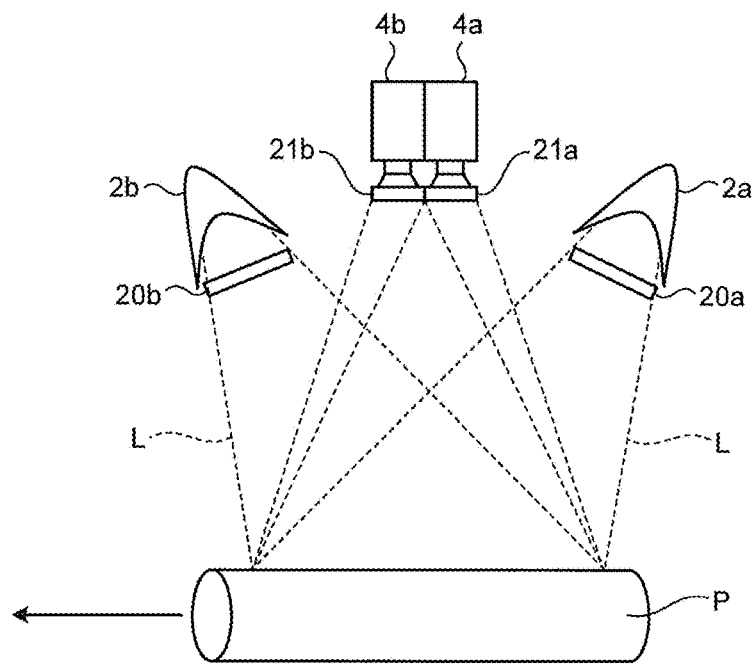
FIG. 7 is a schematic diagram for explanation of surface defect detection processing according to a second structure.

In this modified example, a dichroic mirror is used instead of the wavelength selection filters 21a and 21b arranged at the area sensors 4a and 4b in the surface defect detecting apparatus illustrated in FIG. 7. The dichroic mirror is a mirror that reflects light of a specific wavelength component and transmits light of other wavelength components. By use of the dichroic mirror, wavelength selection filters become unnecessary. Although the illumination light beams are emitted from two directions in this modified example, the same applies to a case where illumination light beams are emitted from not less than three directions.

Second Structure

Next, by referring to FIG. 14A to FIG. 22, a configuration and operation of a surface defect detecting apparatus according to the second structure will be described. Since the configuration of the surface defect detecting apparatus according to this structure is the same as the configuration of the surface defect detecting apparatus according to the above described first structure, hereinafter, description of the configuration will be omitted, and only the operation of the surface defect detecting apparatus will be described.

By executing surface defect detection processing described below, the surface defect detecting apparatus 1 according to the second structure distinguishes a concavo-convex surface defect from scale or a harmless pattern in an examination target part. Scale or a harmless pattern means a portion having a surface film or surface characteristics with optical properties different from those of a base steel portion of a thickness of about several μm to several tens of and is a portion that becomes a cause of noise in the surface defect detection processing.

Surface Defect Detection Processing

In surface defect detection processing according to one of the structures after executing image processing such as calibration, shading correction, noise removal, and the like by use of camera parameters derived in advance for two two-dimensional images input from the area sensors 4a and 4b, the image processing device 5 generates a subtraction image by executing subtraction processing between the two-dimensional images, and detects, from the generated subtraction image, a concavo-convex surface defect in an examination target part.

Specifically, if a luminance value of each pixel constituting a two-dimensional image Ia obtained when the illumination light beam L is emitted from the light source 2a is Ia(x, y) (where the number of pixels is X×Y, the x-coordinate is $1 \leq x \leq X$, and the y-coordinate is $1 \leq y \leq Y$) and a luminance value of each pixel constituting a two-dimensional image Ib obtained when the illumination light beam L is emitted from the light source 2b is Ib(x, y), a luminance value I_diff(x, y) of each pixel of their subtraction image I_diff obtained by subtraction processing is expressed by numerical expression (1) already mentioned.

Figure 4:
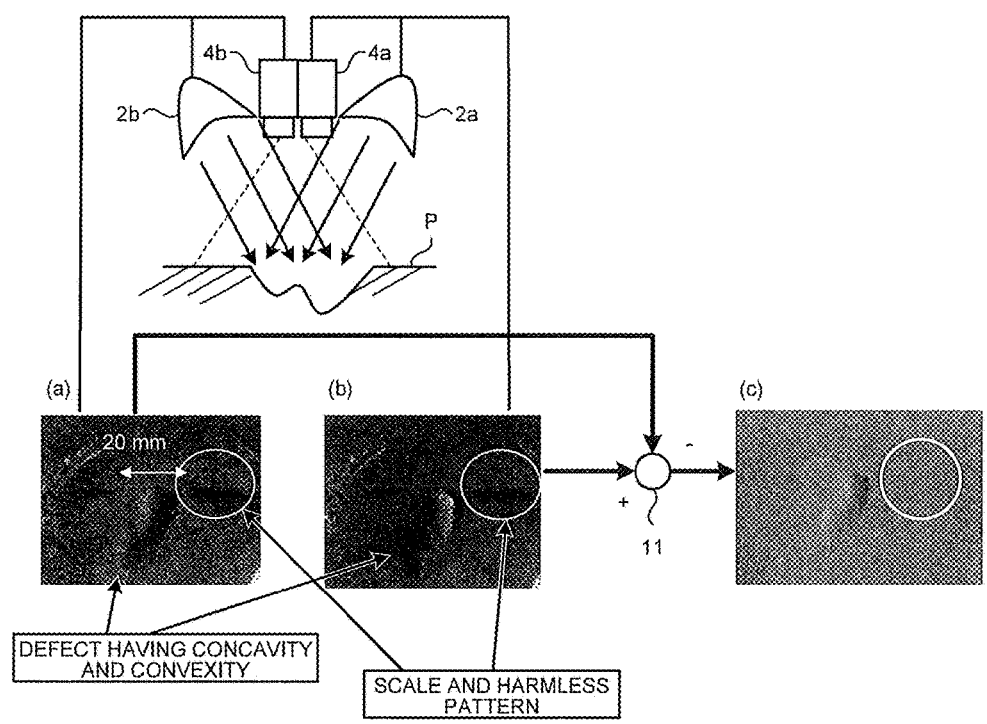
FIG. 4 is a diagram illustrating an example of: two two-dimensional images capturing a surface defect, and scale and a harmless pattern; and a subtraction image thereof.

As illustrated in FIG. 4, in a sound portion, regardless of presence or absence of scale or a harmless pattern, since the angle formed between the normal vector of the surface and the light source 2a equals the angle formed between the normal vector of the surface and the light source 2b, the luminance value Ia(x, y)=the luminance value Ib(x, y), that is, the luminance value I_diff(x, y)=0. However, in a concavo-convex surface defect portion, since the surface has a concavo-convex shape, a site where the angle formed between the normal vector of the surface and the light source 2a does not equal the angle formed between the normal vector of the surface and the light source 2b is always present, and thus the luminance value Ia(x, y)≠the luminance value Ib(x, y), that is, the luminance value I_diff(x, y)≠0. Therefore, by the subtraction device 11 generating the subtraction image I_diff between the two two-dimensional images, an image of scale or a harmless pattern, which is sound and not a surface defect, is able to be removed.

Next, logic of detecting a concavo-convex surface defect from the subtraction image I_diff will be described. FIGS. 14A and B are diagrams respectively illustrating shade and shadow when an examination target part is irradiated with the illumination light beam from one of the light sources when a surface shape of the examination target part is concave shaped and convex shaped. As illustrated in FIG. 14A, when the surface shape of the examination target part is concave shaped, the side near the light source becomes dark due to reduction in light quantity of irradiation light per unit area, and the side far from the light source becomes bright due to the approach to a normal reflection direction. In contrast, as illustrated in FIG. 14B, when the surface shape of the examination target part is convex shaped, the side near the light source becomes bright due to the approach to a normal reflection direction and the side far from the light source becomes dark due to a shadow of the convex shape.

In other words, brightness patterns of reflected light beams of the illumination light beams are different between when the surface shape of the examination target part is concave shaped and when the surface shape is convex shaped. Therefore, by recognition of the brightness pattern of the reflected light beam, presence or absence of a concavo-convex surface defect is able to be detected. Thus, hereinafter, a method of detecting a concavo-convex surface defect by recognizing a brightness pattern of a reflected light beam will be described. Hereinafter, a concave shaped surface defect will be detected, of concavo-convex surface defects, but a convex shaped surface defect may be detected according to similar logic. Further, a bright portion mentioned below means a blob having an area not smaller than a predetermined value obtained by execution of connection processing with respect to pixels having luminance not smaller than a predetermined threshold in the subtraction image I_diff. Further, a dark portion mentioned below refers to a blob, which has an area not smaller than a predetermined value obtained by execution of connection processing with respect to pixels having luminance not greater than a predetermined threshold in the subtraction image I_diff. A blob means a collection of labelled pixels.

In this structure, a brightness pattern is recognized by extraction of a bright portion and a dark portion through execution of threshold processing. Specifically, in the surface defect detecting apparatus 1 according to this structure, since the light sources 2a and 2b are arranged to be left-right symmetrical to each other about a normal vector of an examination target part, a brightness pattern of reflected light resulting from a concavo-convex shape of the surface is generated in a left-right direction. Left and right of brightness is reversed according to the order of subtraction processing, and thus, herein, when the right is bright and the left is dark, the surface is concave shaped and when the right is dark and the left is bright, the surface is convex shaped. Therefore, the subtraction image I_diff of the convex shaped surface defect becomes like the one illustrated in FIG. 15. When images of the bright portion and dark portion are binarized respectively with luminance thresholds The and −The, binarized images I_blight and I_dark of the bright portion and dark portion are respectively expressed by numerical expressions (4):

$$I\_blight(x,y)=1 \text{(When } I\_diff(x,y) \geq \text{The)}$$

$$I\_blight(x,y)=0 \text{(When } I\_diff(x,y) < \text{The)}$$

$$I\_dark(x,y)=1 \text{(When } I\_diff(x,y) \leq -\text{The)}$$

$$I\_dark(x,y)=0 \text{(When } I\_diff(x,y) > -\text{The)} \quad (4).$$

After binarizing the images of the bright portion and dark portion as described above and, as necessary, executing connection and isolated point removal, by calculating a positional relation between the bright portion and dark portion, presence or absence of a concavo-convex surface defect is detected. There are various methods of calculating the positional relation between the bright portion and dark portion and, hereinafter, three representative calculation methods will be described, but any other method enabling calculation of the positional relation between the bright portion and dark portion may be adopted.

Figure 16:
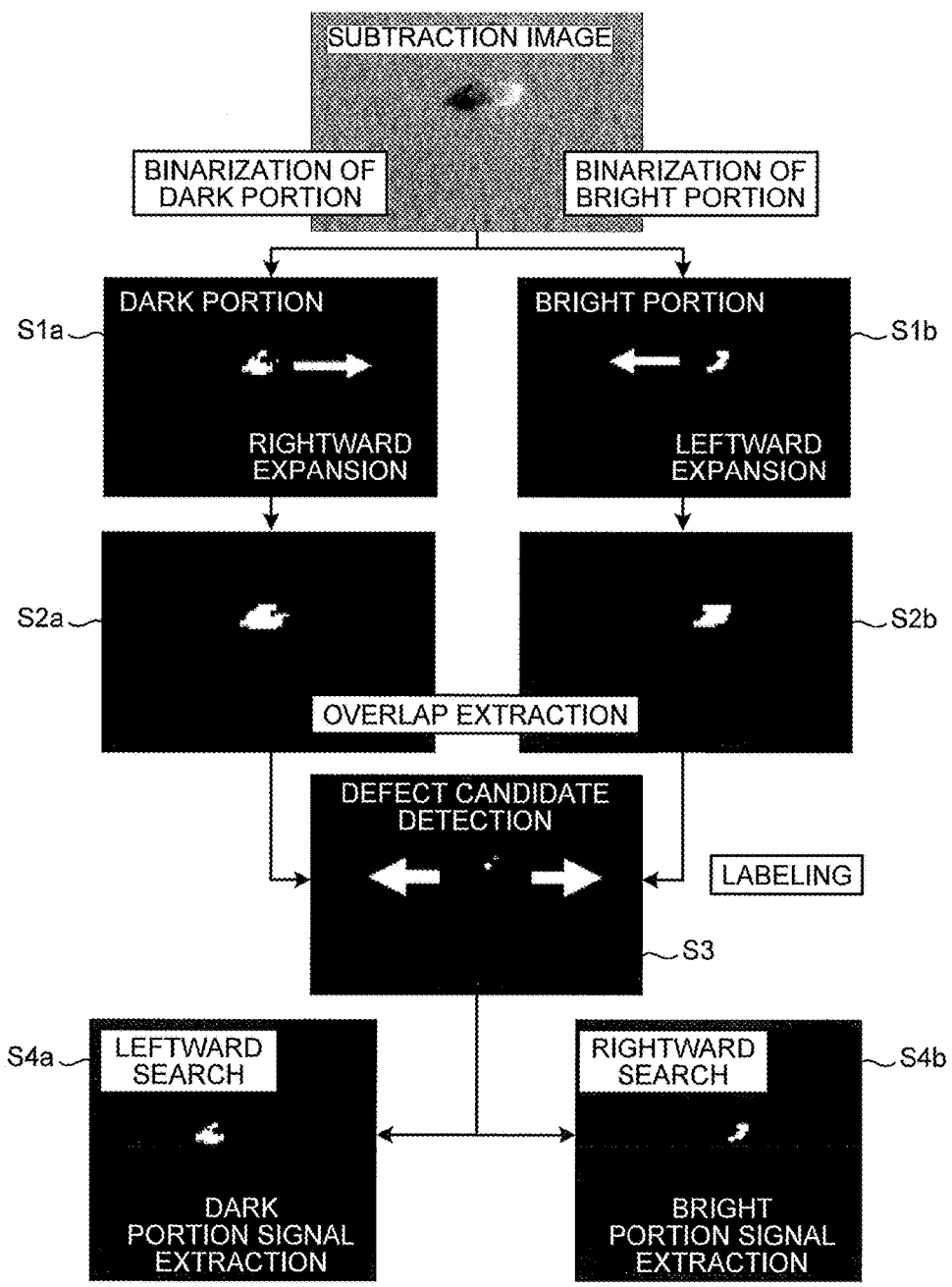
FIG. 16 is a flow chart illustrating a flow of a method of calculating a positional relation between a bright portion and a dark portion by utilization of expansion processing.

A first positional relation calculation method is a method of calculating the positional relation between the bright portion and dark portion by execution of expansion and contraction processing in a specific direction with respect to the bright portion and dark portion. A flow chart of this calculation method is illustrated in FIG. 16. In this method, since a concave shaped surface defect is detected, a case, where a brightness pattern with the right bright and the left dark is recognized, will be described. The right being bright and the left being dark mean that there is always the dark portion on the left side of the bright portion and there is always the bright portion on the right side of the dark portion. In this calculation method, first, the image processing device 5 executes expansion processing in the right direction with respect to the dark portion and executes expansion processing in the left direction with respect to the bright portion (Steps S1a and S1b). When images of the bright portion and dark portion that have been subjected to the expansion processing are respectively denoted as I_blight_extend and I_dark_extend, and the expanded length is W, the expansion processing is expressed by numerical equations (5). With the top left of the two-dimensional image being the origin, the downward direction is positive along a y-axis direction and the rightward direction is positive along an x-axis direction.

$$I\_blight\_extend(x1,y)=1 \ x-W \leq x1 \leq x \text{(When } I\_blight(x,y)=1\text{)}$$

$$I\_dark\_extend(x1,y)=1 \ x \leq x1 \leq x+W \text{(When } I\_dark(x,y)=1\text{)} \quad (5)$$

In this method, although the bright portion and dark portion are expanded by the same length W, the expanded length W is not necessarily the same, and to be extreme, expansion processing may be executed with respect to only one of the bright portion and dark portion. Further, the expanded length W also depends on the size of the surface defect desired to be detected.

Next, by executing AND processing with respect to the images I_blight_extend and I_dark_extend of the bright portion and dark portion that have been subjected to the expansion processing as expressed by numerical equation (6), the image processing device 5 extracts a defect candidate portion image I_defect, which is an overlapping portion between the images I_blight_extend and I_dark_extend of the bright portion and dark portion that have been subjected to the expansion processing (Steps S2a and S2b).

$$I\_defect=I\_blight\_extend \& I\_dark\_extend \quad (6)$$

Next, after executing connection and isolated point removal processing as necessary with respect to each defect candidate portion image I_defect obtained, the image processing device 5 generates a defect candidate blob I_defect_blob by executing labeling processing (Step S3). The image processing device 5 extracts a feature amount of each defect candidate blob I_defect_blob, and determines, based on a result of the extraction, whether or not each defect candidate blob I_defect_blob is a concave shaped surface defect (Steps S4a and S4b). Investigating the feature amount of the defect candidate blob I_defect_blob requires information of the bright portion and dark portion, and thus the bright portion and dark portion are restored from the defect candidate blob I_defect_blob.

Specifically, since a bright portion is always present on the right side of a defect candidate portion and a dark portion is always present on the left side thereof, the image processing device 5 searches the dark portion binarized image I_dark to the left with the center of gravity of the defect candidate blob I_defect_blob being a starting point, and regards a blob that is found first as a dark portion defect candidate blob I_dark_blob. Similarly, the image processing device 5 searches the bright portion binarized image I_blight to the right with the center of gravity of the defect candidate blob I_defect_blob being a starting point, and regards a blob found first as a bright portion defect candidate blob I_blight_blob. The image processing device 5 extracts feature amounts from the bright portion defect candidate blob I_blight_blob and dark portion defect candidate blob that have been restored as described above, and determines, based on the extracted feature amounts, whether or not each defect candidate blob I_defect_blob is a concave shaped surface defect. Specific feature amounts differ according to defects and thus without mentioning the specific feature amounts herein, an example thereof will be described in a later described example.

In a second positional relation calculation method, after the above described threshold processing is executed and as necessary, connection and isolated point removal processing is executed; a bright portion and a dark portion are extracted, labeling is executed, and a positional relation between the bright portion and the dark portion is recognized, to thereby detect a concave shaped surface defect. Specifically, firstly, the image processing device 5 recognizes a bright portion and a dark portion individually by labeling, and obtains center of gravity information of the bright portion and dark portion. Next, the image processing device 5 determines, from the center of gravity information of the bright portion and dark portion, whether or not the center of gravity of the dark portion is present in a predetermined range on a right side of each bright portion. If the center of gravity of the dark portion is present therein, the image processing device 5 recognizes the combination of the bright portion and dark portion forming a pair as a brightness pattern, and determines whether or not it is a concave shaped surface defect, by executing feature mount analysis of the brightness pattern. Although the brightness pattern is recognized by use of the center of gravity information herein, information used in the recognition of the brightness pattern is not necessarily the center of gravity information as long as the information enables positions of the bright portion and dark portion to be grasped (for example, their upper end positions, lower end positions, and the like).

Figure 17A:
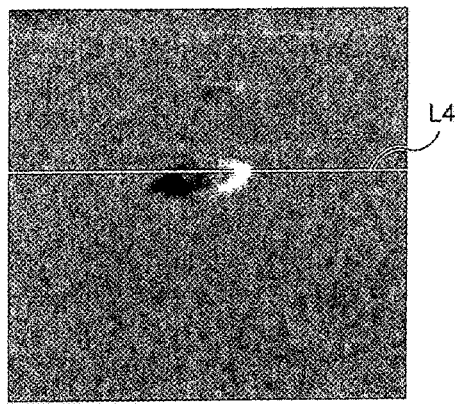
FIGS. 17A and B are diagrams illustrating the subtraction image and a one-dimensional profile of a brightness pattern.
Figure 17B:
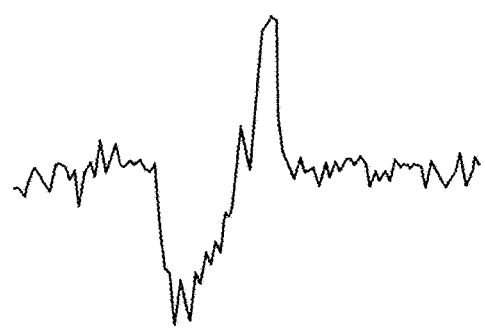

In a third positional relation calculation method, without executing the above described threshold processing, by recognizing a brightness pattern by use of a filter, a concave shaped surface defect is detected. Specifically, in the surface defect detecting apparatus 1 illustrated in FIG. 1, since the light sources 2a and 2b are arranged left-right symmetrically about a normal line of an examination target part, a brightness pattern caused by concavity and convexity of a surface thereof is generated in the left-right direction. FIGS. 17A and B are diagrams respectively illustrating an example of a subtraction image, and a one-dimensional profile of a brightness pattern on a line segment L4 illustrated in FIG. 17A.

As illustrated in FIGS. 17A and B, for a concave shaped surface defect, the right is bright and the left is dark, and thus the one-dimensional profile of the brightness pattern becomes a characteristic one-dimensional profile, in which the right side is mountain shaped and the left side is valley shaped. Thus, in this structure, a filter H with the right side being mountain shaped and the left side being valley shaped is generated in advance, and by subjecting the subtraction image I_diff to the filter H as expressed by numerical equation (7), a two-dimensional image I_cont with reduced high frequency noise and with only the brightness pattern emphasized is generated.

$$I\_cont = H * I\_diff \quad (7)$$

Figure 18A:
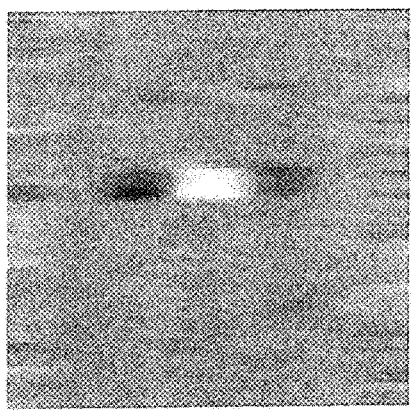
FIGS. 18A and B are diagrams illustrating an example of a two-dimensional image and a one-dimensional profile, of a filter.
Figure 18B:
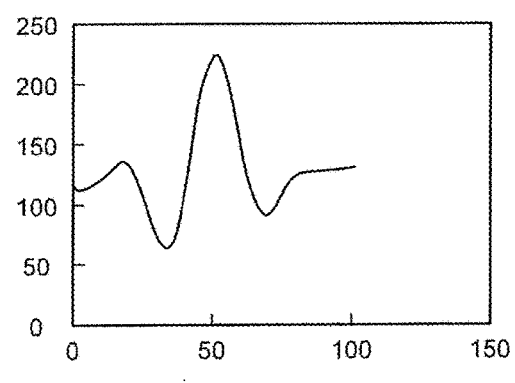
Figure 19A:
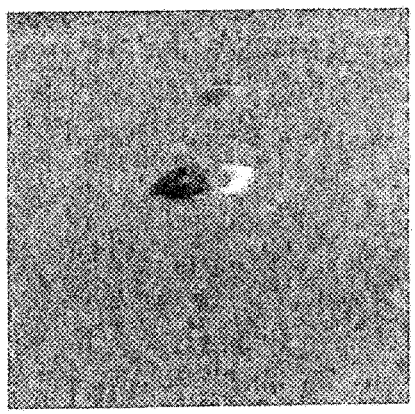
FIGS. 19A and B are diagrams illustrating an example of a subtraction image having been subjected to filtering using the filter illustrated in FIGS. 18A and B and a one-dimensional profile thereof.
Figure 19B:
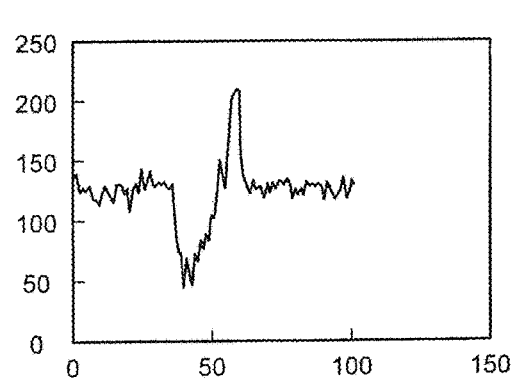

FIGS. 18A and B are diagrams respectively illustrating a two-dimensional image of the filter H generated in advance, and an example of a one-dimensional profile thereof in the left-right direction. FIGS. 19A and B are diagrams respectively illustrating a subtraction image that has been subjected to filtering using the filter H illustrated in FIGS. 18A and B, and a one-dimensional profile thereof in the left-right direction. As illustrated in FIGS. 19A and B, a two-dimensional image with reduced high frequency noise and with only the brightness pattern thereof emphasized is obtained.

As necessary, several types of filters having different ranges in a width direction may be prepared in advance to be compatible with many surface defect sizes. After executing connection and isolated point removal processing as necessary, with respect to the two-dimensional image with its brightness pattern emphasized as described above, the image processing device 5 extracts the defect candidate portion image I_defect by executing threshold processing. The image processing device 5 detects a concave shaped surface defect by executing processing similar to that of the first positional relation calculation method, with respect to the extracted defect candidate portion image I_defect.

As clarified from the above description, in the surface defect detection processing according to one of the structures, the same examination target part is irradiated with the illumination light beams L at approximately the same angle of incidence from different directions by use of the two distinguishable light sources 2a and 2b, the images by the reflected light beams of the respective illumination light beams L are obtained, the bright portion and dark portion of the image obtained by execution of subtraction processing between the obtained images are extracted, and presence or absence of a concavo-convex surface defect is determined from the positional relation between the extracted bright portion and dark portion and the irradiation directions of the illumination light beams L, and thus a concavo-convex surface defect is able to be accurately distinguished from scale or a harmless pattern.

In this structure, although the left and right brightness pattern is recognized since the light sources are arranged left-right symmetrically, even if the arrangement positions of the light sources are not left and right, and are not up-down symmetrical or not symmetrical, a concavo-convex surface defect is able to be detected by similar processing. Specifically, when the light sources are arranged to be up-down symmetrical to each other, since the brightness pattern just changes from the left-right direction to the up-down direction, if the brightness pattern is rotated by 90 degrees, a concavo-convex surface defect is able to be detected by similar processing.

Figure 20:
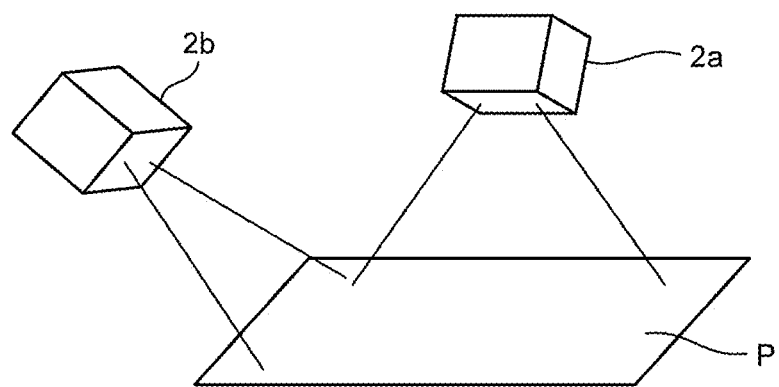
FIG. 20 is a schematic diagram illustrating a modified example of arrangement positions of light sources.
Figure 21A:
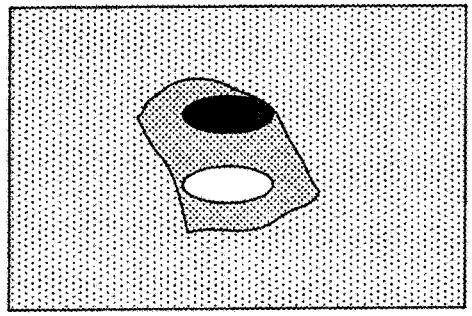
FIGS. 21A, B and C are schematic diagrams illustrating brightness patterns obtained by the arrangement positions of the light sources illustrated in FIG. 20.
Figure 21B:
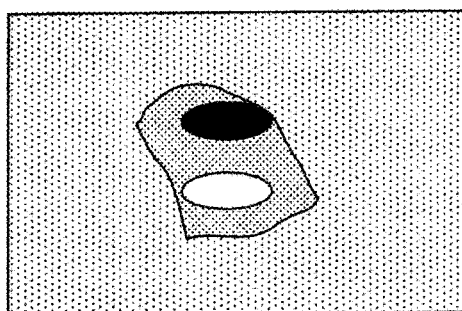
Figure 21C:
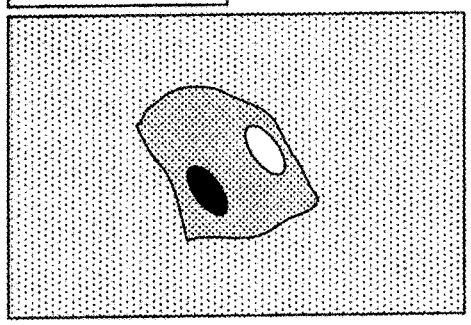

Further, as illustrated in FIG. 20, when the light sources 2a and 2b are arranged such that irradiation directions of the illumination light beams differ from each other by 90 degrees, if the surface defect is concave shaped, the side near the light sources becomes dark and the side far from the light sources becomes bright, and if the surface defect is convex shaped, the side near the light sources becomes bright and the side far from the light sources becomes dark. Specifically, if the surface defect is concave shaped, a two-dimensional image obtained by the illumination light beam from the light source 2a is as illustrated in FIG. 21A, and a two-dimensional image obtained by the illumination light beam from the light source 2b is as illustrated in FIG. 21B. Therefore, the subtraction image has a brightness pattern with a contrast from the lower left to the upper right, as illustrated in FIG. 21C. Thus, if the brightness pattern is rotated by 45 degrees, by a method similar to that for the left-right direction brightness pattern, a concave shaped surface defect is able to be detected. Further, since subtraction images of plural patterns are able to be respectively obtained by use of three or more light sources, accuracy of surface defect detection is able to be improved even more.

Further, in this structure, although a concavo-convex surface defect is detected for when the illumination light beams are emitted from the directions symmetrical about the normal line of the examination target part, the irradiation directions of the illumination light beams are not necessarily symmetrical. Furthermore, the surface defect detection processing according to this structure is applicable to manufacturing lines in general for steel materials regardless of whether they are hot or cold.

Example

In this example, surface defect detection processing using the above described first positional relation calculation method was applied to an examination target part, where a pit defect had been formed and to a sound examination target part, where a pit defect had not been formed. In this example, as feature amounts, a luminance ratio, an area ratio, and circularities of a bright portion and a dark portion were calculated. The circularities are values obtained by division of areas of the bright portion and dark portion by squares of lengths of their circumferences and normalization, and are used in determining whether or not shapes of the bright portion and dark portion are close to a circular shape. If the cause is the same among surface defects, luminances and areas are not likely to be significantly different from one another in the left and right signals, and accuracy of surface defect detection is improved by evaluating the left-right balance by use of the luminance ratio and area ratio. Further, since shade and shadow are evaluated, the bright portion and dark portion hardly become circular shaped, and since those close to a circular shape are able to be determined to be due to a different cause, circularities were included in the feature amounts. Further, areas of the bright portion and dark portion were calculated, and only any surface defect with an area not smaller than a predetermined value was made detectable. Results of the detection are illustrated in FIG. 22. As illustrated in FIG. 22, according to this structure, a pit defect, and a sound portion, where a pit defect is not formed, were confirmed to be accurately distinguishable from each other.

Third Structure

Next, by referring to FIG. 23 to FIG. 26, a configuration and operation of a surface defect detecting apparatus according to the third structure will be described. Since the configuration of the surface defect detecting apparatus according to this structure is the same as the configurations of the surface defect detecting apparatuses according to the above described first and second structures, hereinafter, description of the configuration will be omitted, and only the operation of the surface defect detecting apparatus will be described.

By executing surface defect detection processing described below, the surface defect detecting apparatus 1 according to the third structure distinguishes a concavo-convex surface defect from scale or a harmless pattern in an examination target part. Scale or a harmless pattern means a portion having a surface film or surface characteristics with optical properties different from those of a base steel portion of a thickness of about several μm to several tens of μm, and is a portion that becomes a cause of noise in the surface defect detection processing.

Surface Defect Detection Processing

Figure 23:
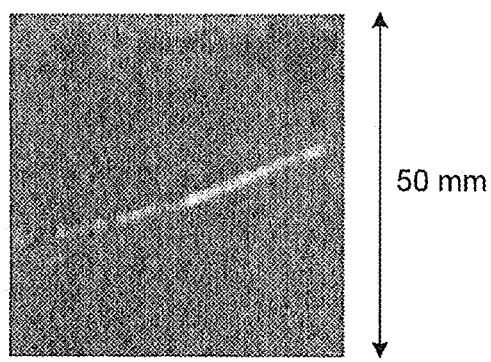
FIG. 23 is a diagram illustrating an example of a linear elongated defect where a brightness pattern of reflected light is not formed.

The surface defect detecting apparatus 1 according to the above described second structure detects a concavo-convex surface defect by recognizing a brightness pattern of reflected light. However, depending on the shape or position of a surface defect, the brightness pattern of the reflected light may be unable to be generated. Specifically, particularly when the normal vector direction at the surface of the steel pipe is largely different from the optical axis direction of the area sensor and the shape of the surface defect is elongated as illustrated in FIG. 23, one of the bright portion and dark portion is hidden from the field of view and only the other one of the bright portion and dark portion is detected, and thus the brightness pattern of the reflected light may be unable to be generated.

Figure 24:
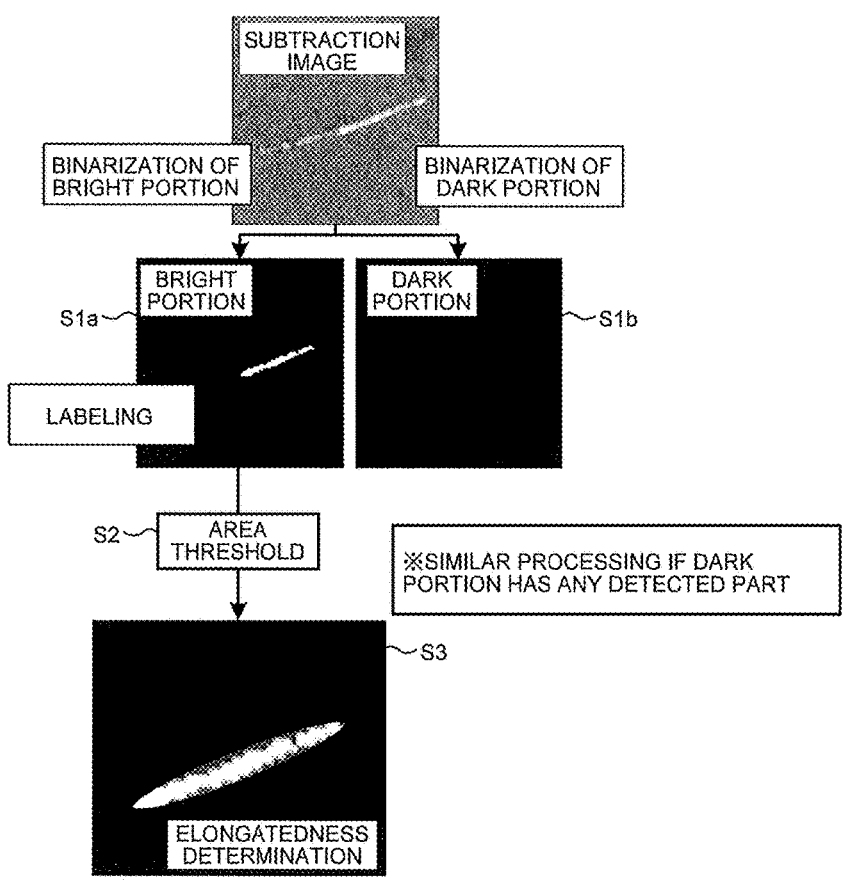
FIG. 24 is a flow chart illustrating a flow of detection processing for an elongated defect according to one method.

Accordingly, separately from the logic of detecting a concavo-convex surface defect by the recognition of a brightness pattern of reflected light, the surface defect detection processing according to one of the methods has logic of detecting an elongated defect by recognition of a shape of a surface defect. An elongated defect mentioned herein means a surface defect having a linear elongated shape characteristic. FIG. 24 is a flow chart illustrating a flow of detection processing for an elongated defect according to an example of our methods. In this method, a surface defect to be detected is a concave shaped elongated defect, but a convex shaped elongated defect may also be detected by this detection processing if only the other one of the bright portion and dark portion is detected.

In the surface defect detection processing according to one of the methods, first, after binarizing a subtraction image between a bright portion and a dark portion with a predetermined luminance threshold, and as necessary, executing connection and isolated point removal, the image processing device 5 executes labeling processing on images of the bright portion and dark portion (Steps S1$a$ and S1$b$). Next, the image processing device 5 extracts images of a bright portion and a dark portion having areas not smaller than a predetermined threshold, from the labeling processed images of the bright portion and dark portion (Step S2). The image processing device 5 then calculates a shape feature amount of a surface defect, which becomes an index of elongatedness, for the extracted images of the bright portion and dark portion, and detects, based on the calculated shape feature amount of the surface defect, an elongated defect (Step S3).

Figure 25A:
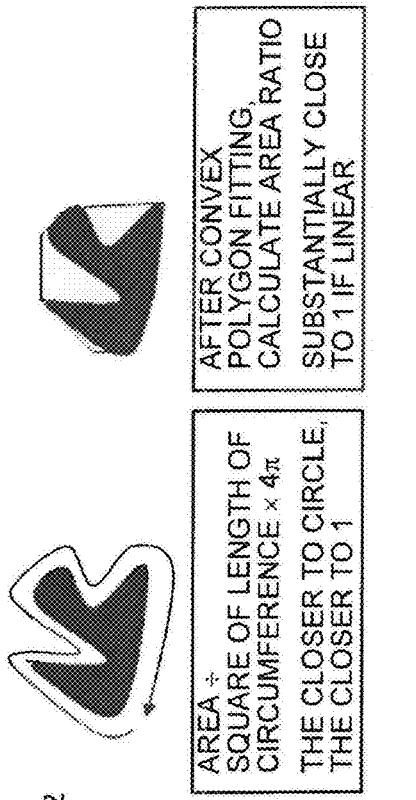
FIGS. 25A, B and C are diagrams for explanation of an example of shape feature amounts of surface defects.

Examples of shape feature amounts of a surface defect, the shape feature amounts becoming indices of elongatedness, include a major axis-minor axis ratio of an ellipse, a maximum Feret's diameter, a circularity, and a convex polygon filling rate. Specifically, if a major axis-minor axis ratio is calculated as a shape feature amount, as illustrated in FIG. 25A, first, the image processing device 5 fits an ellipse R to an image of a bright portion or dark portion. Methods of fitting an ellipse to an image include the least squares method, the secondary moment derivation method and the like, but in consideration of the calculation time, the secondary moment derivation method is more useful. The image processing device 5 calculates lengths of a major axis L1 and a minor axis L2 of the fitted ellipse R, and obtains a ratio between the calculated major axis L1 and minor axis L2 as a shape feature amount.

Figure 25B:
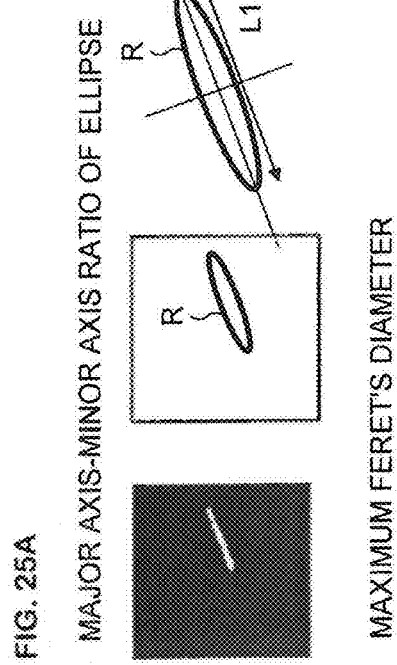

A Feret's diameter is, as illustrated in FIG. 25B, a length L3 of a map obtained when an image of a bright portion or dark portion is orthographically projected one-dimensionally. If a maximum Feret's diameter is calculated as a shape feature amount, firstly, the image processing device 5 calculates, as the maximum Feret's diameter, the maximum value of the length of the orthographic projection while rotating the image of the bright portion or dark portion by 180 degrees. The image processing device 5 then finds, as a shape feature amount, a ratio between a Feret's diameter in a direction orthogonal to a site, for which the maximum Feret's diameter has been calculated, and the maximum Feret's diameter.

Figure 25C:
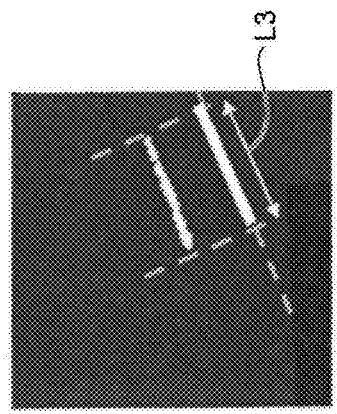

Further, as illustrated in FIG. 25C, a circularity means a value normalized such that the closer the shape of the bright portion or dark portion is to a circle, the closer to 1 a value obtained by dividing an area of the bright portion or dark portion by a square of a length of a circumference of the bright portion or dark portion becomes. Furthermore, a convex polygon filling rate means an area rate of a bright portion or dark portion with respect to an area of a polygon circumscribing the bright portion or dark portion, and the more linear the bright portion or dark portion is, the more closer to 1 the value thereof becomes. Therefore, if the circularity of the bright portion or dark portion is low, and the convex polygon filling rate is high on the contrary, the shape of that bright portion or dark portion is able to be determined to be elongated shaped.

When an elongated defect is detected, by considering, not only a shape feature amount of the surface defect, but also a direction of the surface defect such as a vertical direction, a horizontal direction, or a diagonal direction, accuracy of detection for the elongated defect is able to be improved. For example, a direction of a surface defect is able to be checked by finding: a direction in which the major axis is oriented if the major axis-minor axis ratio is calculated as a shape feature amount of a surface defect; and a rotation angle of the image of the bright portion or dark portion upon obtainment of the maximum Feret's diameter if the maximum Feret's diameter is calculated as a shape feature amount of the surface defect. Further, although details thereof will be omitted, by subjecting the image to a linear filter emphasizing a specific direction, a direction of a surface defect may also be checked.

Further, in this structure, the light sources are arranged left-right symmetrically about the normal vector of the steel pipe, but even if the arrangement positions of the light sources are not left-right symmetrical about the normal vector of the steel pipe, and is not up-down symmetrical or not symmetrical as illustrated in FIG. 20, for example, an elongated defect is able to be detected by similar detection processing. Furthermore, while scale or a harmless pattern is flat and thus even if the incident direction of the illumination light beam changes, the scale or the harmless pattern looks the same; when the incident light beam of the illumination light beam changes, an elongated defect looks differently, and thus the elongated defect is able to be detected by the above described logic. Moreover, since subtraction images of plural patterns are able to be obtained respectively by use of three or more light sources, accuracy of detection for an elongated defect is able to be improved further.

As clarified from the above description, in the surface defect detection processing according to one of the structures, the same examination target part is irradiated with the illumination light beams L at approximately the same angle of incidence from different directions by use of the two distinguishable light sources 2a and 2b, the images by the reflected light beams of the respective illumination light beams L are obtained, the bright portion and dark portion of the image obtained by execution of subtraction processing between the obtained images are extracted, the shape feature amount that becomes an index of elongatedness of the extracted bright portion and dark portion is calculated, and presence or absence of an elongated defect is determined based on the calculated shape feature amount, and thus the elongated defect is able to be accurately distinguished from scale or a harmless pattern.

Example

In this example, our surface defect detection processing was applied to an examination target part, where an overrun defect had been formed, and to a sound examination target part, where an overrun defect had not been formed. An overrun defect is a surface defect characterized in that the surface defect has a linear elongated shape, and is directed obliquely upward to the right with respect to the rolling direction. Presence or absence of an overrun defect was determined by calculating a major axis-minor axis ratio and a major axis angle as shape feature amounts of a surface defect and comparing the calculated major axis-minor axis ratio and major axis angle with predetermined thresholds. Results of the determination are illustrated in FIG. 26. As illustrated in FIG. 26, according the surface defect detection processing of this method, an overrun defect and a sound portion, where an overrun defect is not formed, were confirmed to be accurately distinguishable from each other.

The structure methods, to which the the contents of disclosure has been applied, have been described above, but the disclosure is not limited by the description and drawings forming a part of disclosure through these structures, methods and examples. That is, any other structures, working examples, operation techniques, and the like implemented by those skilled in the art or the like based on the structures and methods are all included in the scope of this disclosure and the appended claims.

INDUSTRIAL APPLICABILITY

A surface defect detecting method and a surface defect detecting apparatus that enable a surface defect to be accurately distinguished from scale or a harmless pattern, are provided.

The invention claimed is:

1. A method of optically detecting a surface defect of a steel material comprising:
    an irradiation step of irradiating an examination target part with illumination light beams from different directions with two or more distinguishable light sources; and
    a detection step of obtaining images by reflected light beams of the respective illumination light beams and detecting a surface defect in the examination target part by executing subtraction processing between the obtained images, wherein
    the detection step includes a determination step of extracting a bright portion and a dark portion of an image obtained by the execution of subtraction processing between the obtained images, and determining presence or absence of a concavo-convex surface defect from a positional relation between the extracted bright portion and dark portion and irradiation directions of the illumination light beams.

2. The method according to claim 1, wherein the determination step includes a step of executing expansion processing with respect to images of the bright portion and the dark portion, and calculating a positional relation between the bright portion and the dark portion by extraction of an overlapping portion between the images of the bright portion and dark portion that have been subjected to the expansion processing.

3. The method according to claim 1, wherein the determination step includes a step of executing binarization processing and labeling processing with respect to images of the bright portion and the dark portion, and calculating a positional relation between the bright portion and the dark portion by comparing positions of the centers of gravity of the images that have been subjected to the labeling processing.

4. A method of optically detecting a surface defect of a steel material comprising:
   an irradiation step of irradiating an examination target part with illumination light beams from different directions with two or more distinguishable light sources; and
   a detection step of obtaining images by reflected light beams of the respective illumination light beams and detecting a surface defect in the examination target part by executing subtraction processing between the obtained images, wherein
   the detection step includes a determination step of obtaining images by reflected light beams of the respective illumination light beams, extracting a bright portion and a dark portion of an image obtained by executing subtraction processing between the obtained images, calculating a shape feature amount that becomes an index of elongatedness of the extracted bright portion and dark portion, and determining, based on the calculated feature amount, presence or absence of an elongated defect.

5. The method according to claim 4, wherein the determination step includes a step of determining the presence or absence of an elongated defect, based on, in addition to the shape feature amount, a direction of the bright portion and dark portion.

6. A surface defect detecting apparatus that optically detects a surface defect of a steel material, the surface defect detecting apparatus comprising:
   an irradiation unit configured to irradiate an examination target part with illumination light beams from different directions with two or more distinguishable light sources; and
   a detection unit configured to obtain images by reflected light beams of the respective illumination light beams, extract a bright portion and a dark portion of an image obtained by executing subtraction processing between the obtained images, and determine presence or absence of a concavo-convex surface defect from a positional relation between the extracted bright portion and dark portion and irradiation directions of the illumination light beams.

7. A surface defect detecting apparatus that optically detects a surface defect of a steel material, the surface defect detecting apparatus comprising:
   an irradiation unit configured to irradiate an examination target part with illumination light beams from different directions with two or more distinguishable light sources; and
   a detection unit configured to obtain images by reflected light beams of the respective illumination light beams, extract a bright portion and a dark portion of an image obtained by executing subtraction processing between the obtained images, obtain a shape feature amount that becomes an index of elongatedness of the extracted bright portion and dark portion, and determine, based on the calculated feature amount, presence or absence of an elongated defect.

* * * * *